(12) United States Patent
Sumino et al.

(10) Patent No.: US 11,084,846 B2
(45) Date of Patent: Aug. 10, 2021

(54) METHOD FOR PRODUCING PEPTIDE

(71) Applicant: Hamari Chemicals, Ltd., Osaka (JP)

(72) Inventors: Fumitoshi Sumino, Osaka (JP); Ayaka Deguchi, Osaka (JP); Rui Ono, Osaka (JP); Yuta Hiroyama, Osaka (JP); Teruhiko Kanno, Osaka (JP); Hiroki Moriwaki, Osaka (JP)

(73) Assignee: Hamari Chemicals, Ltd., Osaka (JP)

( * ) Notice: Subject to any disclaimer, the term of this patent is extended or adjusted under 35 U.S.C. 154(b) by 0 days.

(21) Appl. No.: 16/496,245

(22) PCT Filed: Mar. 29, 2018

(86) PCT No.: PCT/JP2018/013147
§ 371 (c)(1),
(2) Date: Sep. 20, 2019

(87) PCT Pub. No.: WO2018/181679
PCT Pub. Date: Oct. 4, 2018

(65) Prior Publication Data
US 2020/0024305 A1    Jan. 23, 2020

(30) Foreign Application Priority Data
Mar. 31, 2017 (JP) .............................. JP2017-072780

(51) Int. Cl.
*C07K 1/04* (2006.01)
*B01J 8/10* (2006.01)
(Continued)

(52) U.S. Cl.
CPC ................ *C07K 1/045* (2013.01); *B01F 7/32* (2013.01); *B01F 15/063* (2013.01); *B01J 8/10* (2013.01);
(Continued)

(58) Field of Classification Search
CPC ........ B01F 7/32; B01F 7/0015; B01F 7/1625; B01F 7/005; B01F 7/00508;
(Continued)

(56) References Cited

U.S. PATENT DOCUMENTS

| | | | | |
|---|---|---|---|---|
| 1,031,666 A | * | 7/1912 | Richmond | ............ B01F 7/1625 366/265 |
| 1,645,614 A | * | 10/1927 | Monahan | ............. A47J 43/0711 366/265 |

(Continued)

FOREIGN PATENT DOCUMENTS

| | | |
|---|---|---|
| JP | 7-501261 A | 2/1995 |
| JP | 2000-503892 A | 4/2000 |

(Continued)

OTHER PUBLICATIONS

International Search Report for PCT/JP2018/013147 dated Jun. 26, 2018.

(Continued)

*Primary Examiner* — Lessanework Seifu
(74) *Attorney, Agent, or Firm* — Knobbe Martens Olson & Bear LLP

(57) ABSTRACT

An object of the present invention is to provide a novel solid phase peptide synthesis method for synthesizing a large amount of a peptide. Another object of the present invention is to provide a novel solid phase peptide synthesis method for synthesizing a high-purity long-chain peptide. Still another object of the present invention is to provide a novel solid phase peptide synthesis method causing fewer side reactions. The present invention relates to a method for producing a peptide, and the method comprises solid-phase synthesis of a peptide under stirring with a centrifugal stirrer having no impeller.

10 Claims, 12 Drawing Sheets

(51) Int. Cl.
*B01F 7/32* (2006.01)
*B01F 15/06* (2006.01)
*C07K 1/34* (2006.01)
*B01J 19/00* (2006.01)

(52) U.S. Cl.
CPC ............ B01J 19/0066 (2013.01); C07K 1/34 (2013.01); *B01F 2015/062* (2013.01)

(58) Field of Classification Search
CPC .... B01F 7/00541; B01F 7/0055; C07K 1/045; C07K 1/34; B01J 8/10; B01J 19/0046; B01J 19/0066
See application file for complete search history.

(56) References Cited

U.S. PATENT DOCUMENTS

| | | | | |
|---|---|---|---|---|
| 2,635,860 | A * | 4/1953 | McLeod | A47J 43/0705 366/265 |
| 2,718,385 | A * | 9/1955 | Greblick | B01F 7/00558 416/181 |
| 3,170,638 | A * | 2/1965 | Burton | B01F 7/005 241/46.17 |
| 3,951,741 | A * | 4/1976 | Pfaender | B01J 19/0046 435/68.1 |
| 4,138,215 | A * | 2/1979 | Huber | G01N 33/0006 422/116 |
| 4,356,133 | A * | 10/1982 | Cowen | B01J 10/02 264/482 |
| 4,746,490 | A * | 5/1988 | Saneii | B01J 19/0046 422/111 |
| 4,943,164 | A * | 7/1990 | Ohishi | B01F 11/0014 366/110 |
| 5,186,824 | A | 2/1993 | Anderson et al. | |
| 5,272,075 | A | 12/1993 | Anderson et al. | |
| 5,273,656 | A | 12/1993 | Anderson et al. | |
| 5,551,779 | A * | 9/1996 | Gantner | B01F 9/0001 366/217 |
| 6,015,881 | A * | 1/2000 | Kang | C07K 14/005 530/339 |
| 2004/0022122 | A1* | 2/2004 | Kozyuk | B01F 3/1221 366/262 |
| 2004/0085856 | A1* | 5/2004 | Murosako | B01F 7/0045 366/262 |
| 2012/0081990 | A1 | 4/2012 | Murata | |
| 2014/0177379 | A1 | 6/2014 | Hattori | |
| 2015/0225444 | A1 | 8/2015 | Wessman et al. | |
| 2016/0168209 | A1 | 6/2016 | Yoshida et al. | |
| 2016/0199798 | A1 | 7/2016 | Hattori | |
| 2017/0282144 | A1 | 10/2017 | Sugiyama et al. | |
| 2018/0133676 | A1 | 5/2018 | Sugiyama et al. | |

FOREIGN PATENT DOCUMENTS

| | | |
|---|---|---|
| JP | 2014-124540 A | 7/2014 |
| JP | 2015-47540 A | 3/2015 |
| JP | 2015-136682 A | 7/2015 |
| JP | 2015-171695 A | 10/2015 |
| JP | 2015-535810 A | 12/2015 |
| JP | 2016-117005 A | 6/2016 |
| JP | 2017 006897 | 1/2017 |
| WO | WO 97/27940 A1 | 8/1997 |
| WO | WO 2010/150656 A1 | 12/2010 |
| WO | WO 2014/046278 A1 | 3/2014 |
| WO | WO 2015/137411 A1 | 9/2015 |

OTHER PUBLICATIONS

International Preliminary Report on Patentability for PCT/JP2018/013147 dated Oct. 1, 2019.
Extended European Search Report dated Dec. 11, 2020 for EP 18775750.5.

* cited by examiner (a)

(b)

(a)

(b)

METHOD FOR PRODUCING PEPTIDE

CROSS REFERENCE TO RELATED APPLICATIONS

This application is a U.S. National Phase Application of PCT International Application Number PCT/JP2018/013147, filed on Mar. 29, 2018, designating the United States of America and published in the Japanese language, which is an International Application of and claims the benefit of priority to Japanese Patent Application No. 2017-072780, filed on Mar. 31, 2017. The disclosures of the above-referenced applications are hereby expressly incorporated by reference in their entireties.

TECHNICAL FIELD

The present invention relates to a method for producing a peptide. More specifically, the present invention relates to a method for synthesizing a large amount of a long-chain peptide by solid phase synthesis.

BACKGROUND ART

Typical stirring means used in the solid phase synthesis of long-chain peptides include stirring by shaking, stirring by nitrogen bubbling, and stirring by a stirrer.

Centrifugal stirrers are also known (for example, Patent Literature 1 to 4), and in an example, a centrifugal stirrer is used as a member of a liposome production apparatus (Patent Literature 5). However, there has been no report of using a centrifugal stirrer as a member of a solid phase peptide synthesizer in the organic synthesis field.

CITATION LIST

Patent Literature

Patent Literature 1: WO 2010/150656 pamphlet
Patent Literature 2: JP 2014-124540 A
Patent Literature 3: JP 2015-171695 A
Patent Literature 4: JP 2015-47540 A
Patent Literature 5: JP 2016-117005 A

SUMMARY OF INVENTION

Technical Problem

An object of the present invention is to provide at least one solid phase synthesis method selected from a novel solid phase peptide synthesis method of synthesizing a large amount of a peptide, a novel solid phase peptide synthesis method of synthesizing a high-purity long-chain peptide, and a novel solid phase peptide synthesis method causing fewer side reactions.

Solution to Problem

As a result of intensive studies in order to attain the above objects, the inventors of the present invention have found that application of a centrifugal stirrer to solid phase peptide synthesis enables synthesis of a large amount of a high-purity long-chain peptide. The inventors have further studied on the basis of the findings and have completed the present invention.

In other words, the present invention relates to the following aspects.

[1] A method for producing a peptide, the method comprising solid-phase synthesis of a peptide under stirring with a centrifugal stirrer having no impeller.
[2] The production method according to the above [1], wherein the centrifugal stirrer having no impeller is a stirring rotor comprising
   a main body configured to rotate about a rotating shaft,
   an inlet port provided on a surface of the main body,
   an outlet port provided on the surface of the main body, and
   a flow path connecting the inlet port to the outlet port,
   the inlet port is provided closer to the rotating shaft than the outlet port, and
   the outlet port is provided more distant from the rotating shaft in a centrifugal direction than the inlet port.
[3] Use of a centrifugal stirrer having no impeller for solid phase peptide synthesis.
[4] A reaction container for solid phase peptide synthesis, the reaction container comprising a centrifugal stirrer having no impeller.
[5] The reaction container for solid phase peptide synthesis according to the above [4], further comprising a glass filter.

Advantageous Effects of Invention

According to the present invention, at least one solid phase synthesis method selected from a novel solid phase peptide synthesis method of synthesizing a large amount of a peptide, a novel solid phase peptide synthesis method of synthesizing a high-purity long-chain peptide, and a novel solid phase peptide synthesis method causing fewer side reactions (for example, unfavorable side chain deprotection reaction in resin cleavage reaction of a fragment peptide before the final coupling reaction) can be provided.

The reaction in the solid phase synthesis includes protecting group introduction reaction before coupling reaction, activation reaction of a carboxyl group or an amino group contributing to coupling reaction of a peptide before coupling reaction, coupling reaction, resin cleavage reaction, and deprotection reaction after coupling reaction and resin cleavage reaction.

DESCRIPTION OF EMBODIMENTS

The present invention provides a method for producing a peptide, and the method comprises solid-phase synthesis of a peptide under stirring with a centrifugal stirrer having no impeller.

Centrifugal Stirrer Having No Impeller

A centrifugal stirrer having no impeller means, for example, a stirrer itself having no impeller in appearance but having a function of stirring a fluid using centrifugal force. The fluid preferably contains a resin, intended peptide constituent amino acids, or a combination of them. The centrifugal stirrer having no impeller may have, for example, a rotor structure in which an inlet port near a rotating shaft is connected to an outlet port distant from the rotating shaft through a flow path. The stirring principle may be, for example, as follows: rotation of a stirrer generates centrifugal force in a flow path; a fluid is discharged in the lateral direction; a longitudinal flow path has a negative pressure; and a negative pressure suction flow is generated in a lower part.

Figure 1:
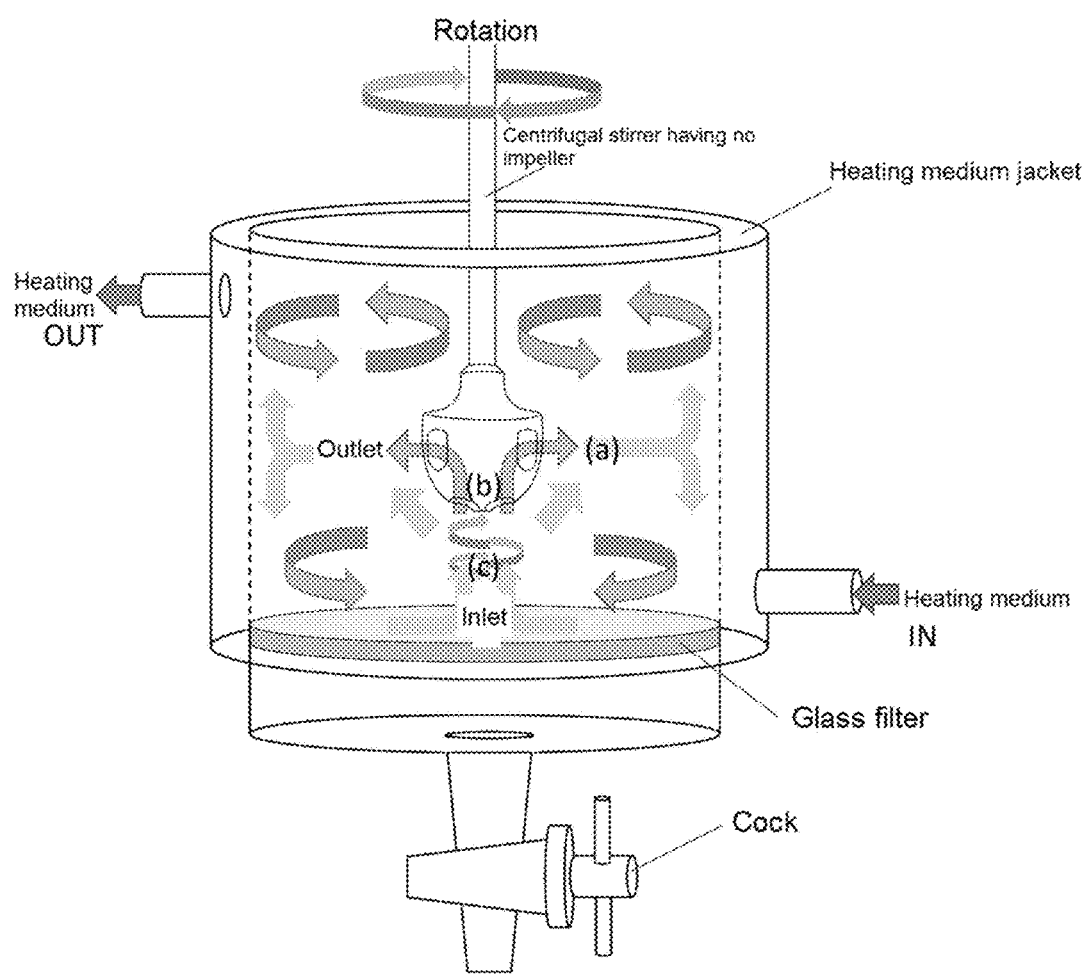
FIG. 1 is a configuration example of a container equipped with a centrifugal stirrer having no impeller.

A configuration example of a container equipped with a centrifugal stirrer having no impeller is shown in FIG. 1. When the centrifugal stirrer having no impeller is rotated, a centrifugal force is generated through outlet ports (a), and a fluid is discharged from the outlet ports (a) in the lateral direction. Accordingly, a suction force is generated in inlet ports (b), and a tornado-like vortex flow (c) is formed. The longitudinal flow paths have a negative pressure to generate a negative pressure suction flow in the downward direction, thus forming a "push and pull" flow. A pulse is transmitted from the centrifugal stirrer having no impeller to a stirring flow, and the stirring flow is spread over the whole container.

As the centrifugal stirrer having no impeller, M-Revo (registered trademark) or E-REVO manufactured by MEDECH Co., Ltd., or the like can be used.

As the centrifugal stirrer having no impeller, for example, the stirrers according to WO 2010/150656 pamphlet, JP 4418019 B, and JP 2014-124540 A may be used.

Figure 2:
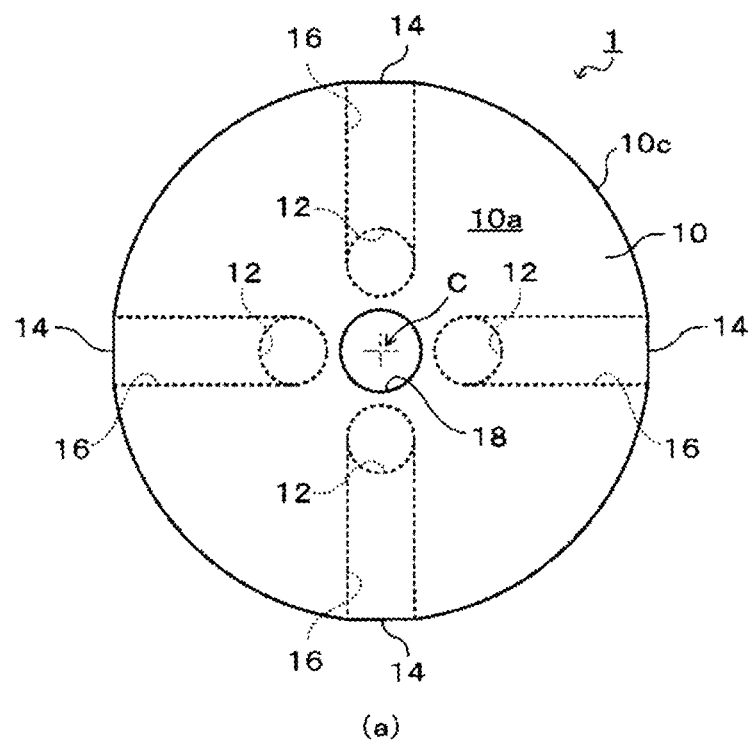
FIG. 2A is a plan view of a stirring rotor pertaining to an embodiment of the present invention.
FIG. 2B is a front view of the stirring rotor (citation of FIG. 1 in JP 4418019 B).
Figure 2:
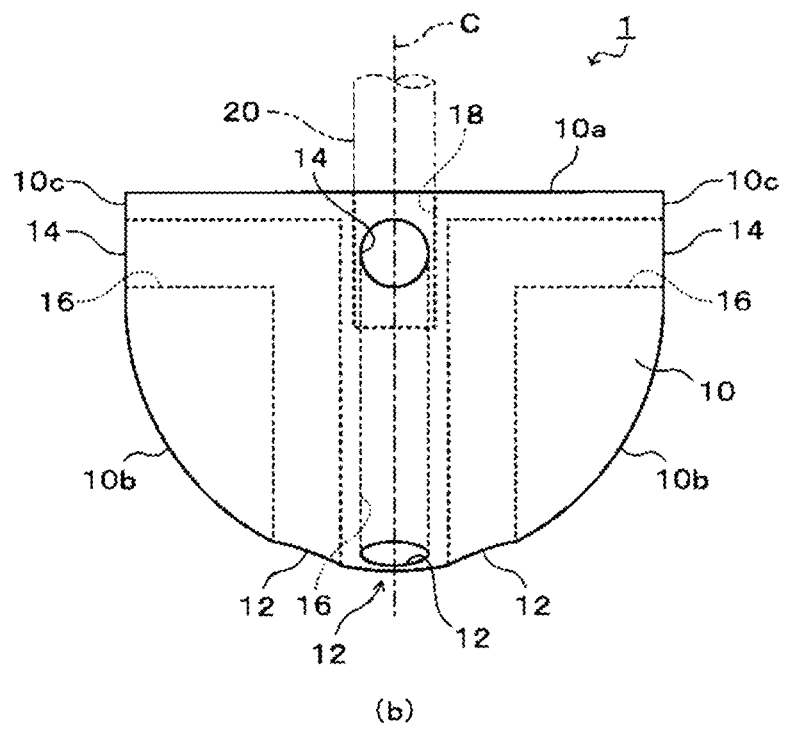
Figure 3:
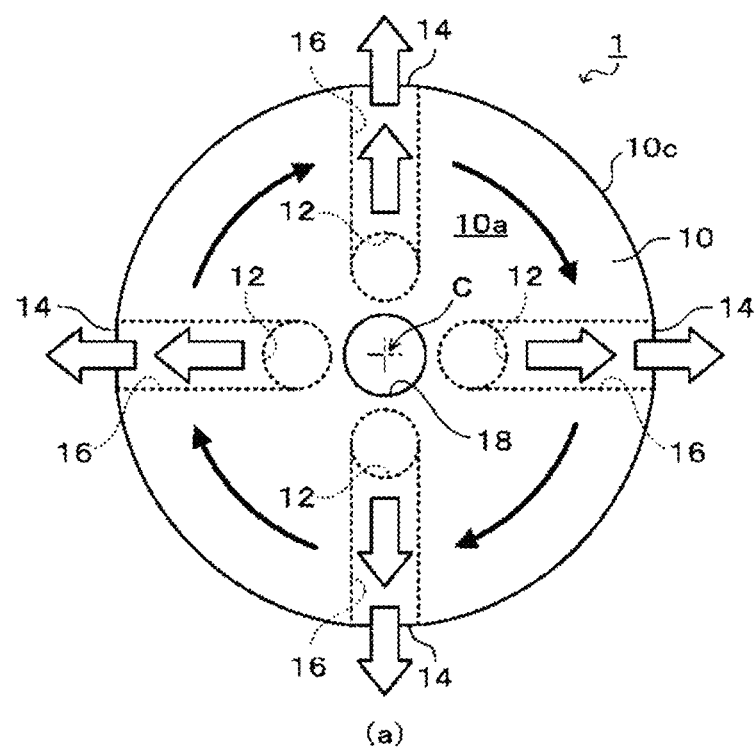
FIG. 3A is a plan view showing an operation of the stirring rotor.
FIG. 3B is a front view showing an operation of the stirring rotor (citation of FIG. 2 in JP 4418019 B).
Figure 3:
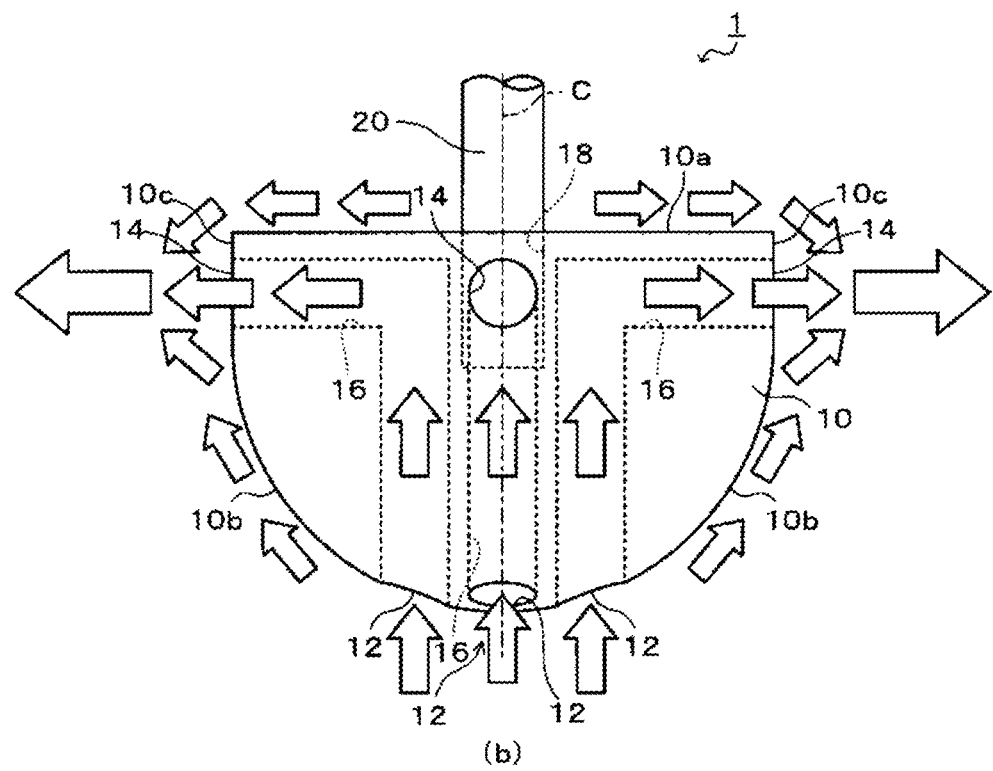
Figure 4:
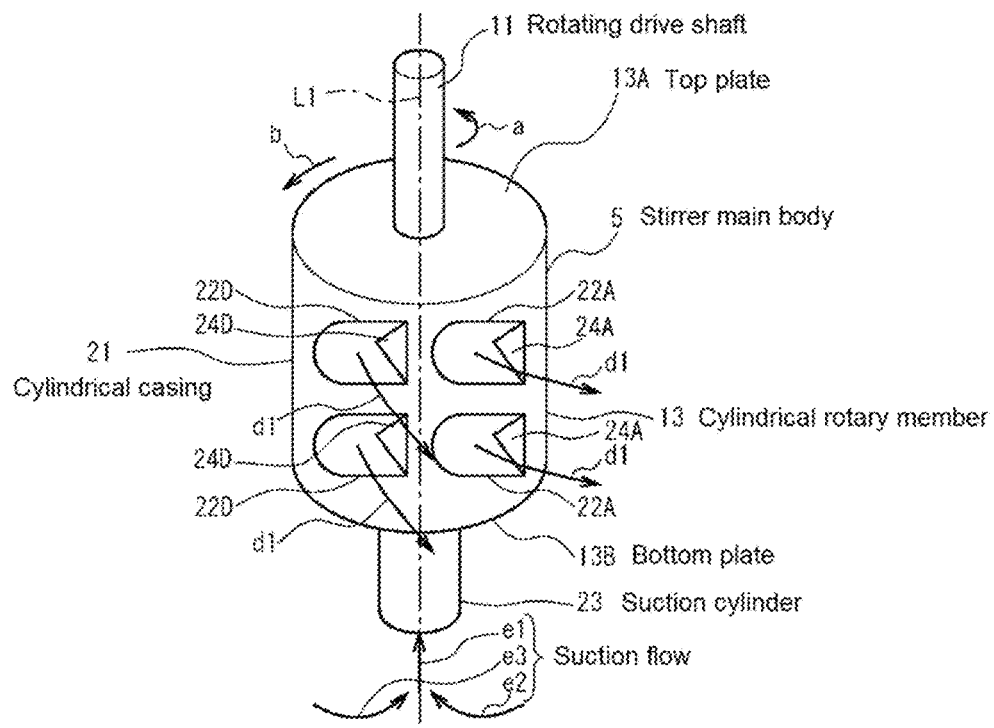
FIG. 4 is a perspective view showing an embodiment of a stirrer main body (citation of FIG. 2 in JP 2014-124540 A, partially modified).
Figure 5:
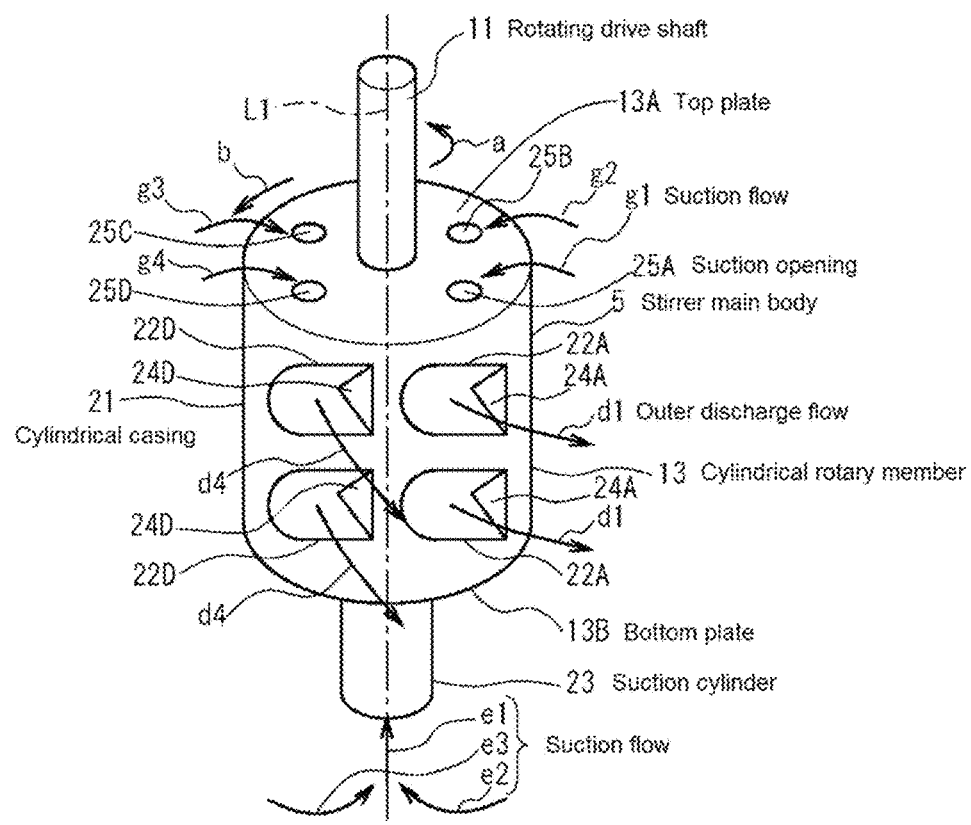
FIG. 5 is a perspective view showing an embodiment of the stirrer main body (citation of FIG. 4 in JP 2014-124540 A, partially modified).
Figure 6:
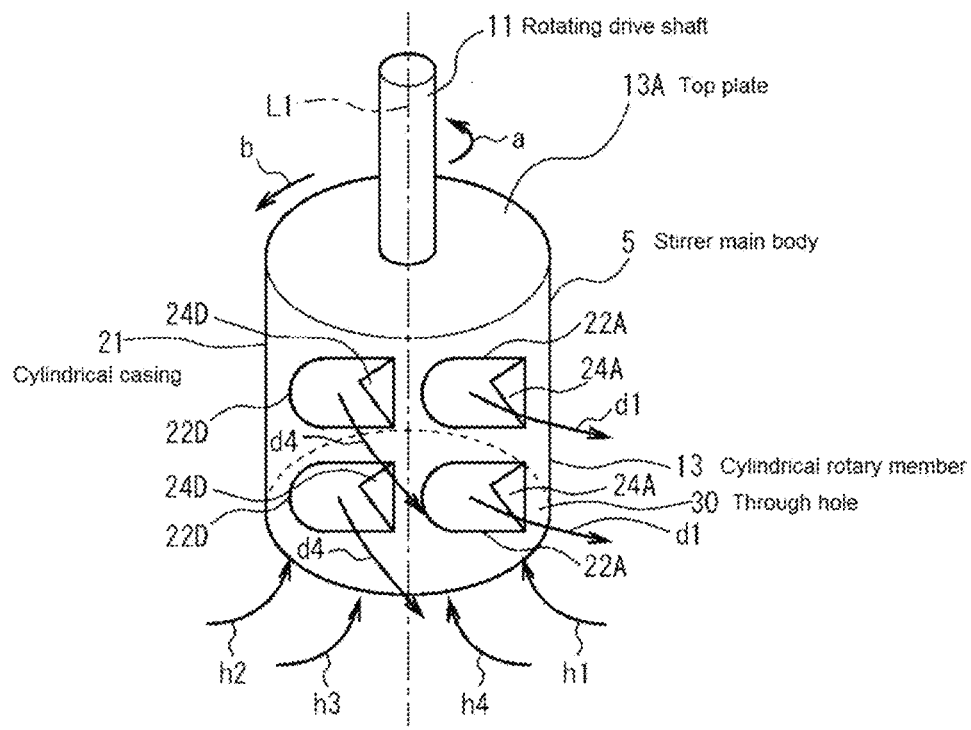
FIG. 6 is a perspective view showing an embodiment of the stirrer main body (citation of FIG. 6 in JP 2014-124540 A, partially modified).

In other words, the centrifugal stirrer having no impeller may be (1) a stirring rotor comprising
a main body configured to rotate about a rotating shaft,
inlet ports provided on the surface of the main body,
outlet ports provided on the surface of the main body, and
flow paths connecting the inlet ports to the outlet ports, in which
the inlet ports are provided closer to the rotating shaft than the outlet ports, and
the outlet ports are provided more distant from the rotating shaft in the centrifugal direction than the inlet ports (for example, see FIGS. 2 and 3), (2) a stirring rotor comprising
a main body having a circular cross-section perpendicular to a rotating shaft direction,
inlet ports provided on the surface of the main body,
outlet ports provided on the surface of the main body, and
flow paths connecting the inlet ports to the outlet ports, in which
the inlet ports are provided closer to the rotating shaft than the outlet ports, and
the outlet ports are provided more distant from the rotating shaft in the radial direction than the inlet ports (for example, see FIGS. 2 and 3), or (3) a stirrer main body comprising a cylindrical rotary member comprising a cylindrical casing having an upper end closed with a top plate, in which the stirrer main body is configured to be rotated by a rotating drive shaft fixed to the top plate, about a central axis of the cylindrical casing,
the cylindrical rotary member comprises
a plurality of discharge openings penetrating the peripheral face of the cylindrical casing,
a plurality of projecting extruded plates provided on the inner peripheral face of the cylindrical casing so as to project inward, and
a suction opening provided on the lower end of the cylindrical casing, and
when rotated, the cylindrical rotary member generates, by means of the projecting extruded plates, an inner circulation flow that circulates an internal stirring liquid about the central axis, then discharges a part of the stirring liquid contained in the inner circulation flow by centrifugal force from the discharge openings as an outer discharge flow to the outside, and incorporates an external stirring liquid from the suction opening as a suction flow into the inside (for example, see FIGS. 4 to 6).

Stirring Conditions

As the stirring apparatus, a container equipped with the above stirrer can be used, for example. "Being equipped" means integration as a part of an apparatus, for example.

Figure 7:
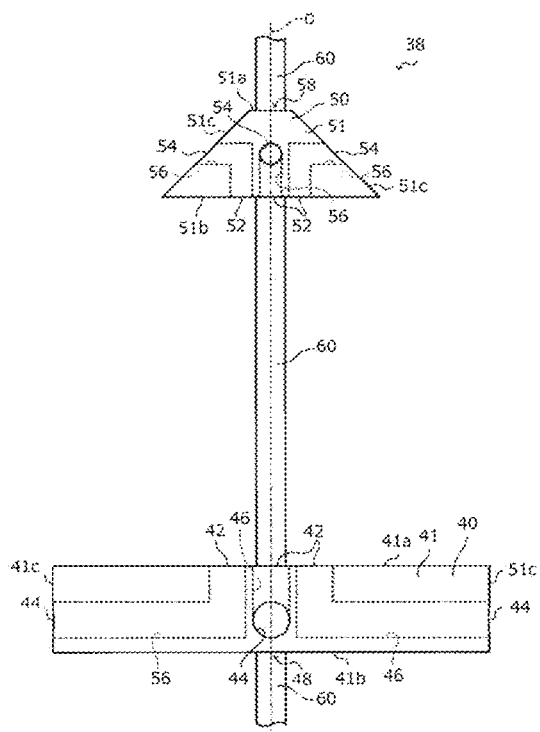
FIG. 7 is a front view (side view) showing an embodiment of a stirring apparatus (citation of FIG. 1 in JP 2015-171695 A, partially modified).

The stirring apparatus may be
a stirring apparatus comprising a stirring rotor and a flow resistor that are adjacent to each other, in which
the stirring rotor comprises
a main body configured to rotate about a rotating shaft,
inlet ports provided on the surface of the main body,
outlet ports provided on the surface of the main body, more distant from the rotating shaft in the centrifugal direction than the inlet ports, and
flow paths connecting the inlet ports to the outlet ports,
the flow resistor comprises
a resistor main body configured to rotate about a resistor rotating shaft, resistor inlet ports provided on the surface of the resistor main body, resistor outlet ports provided on the surface of the resistor main body, more distant from the resistor rotating shaft in the centrifugal direction than the resistor inlet ports, and resistor flow paths connecting the resistor inlet ports to the resistor outlet ports, and the resistor main body is different in shape or size from the main body of the stirring rotor or has a posture different from that of the main body of the stirring rotor (for example, see FIG. 7) (see JP 2015-171695 A).

The above stirring apparatus is useful as a reaction container for solid phase peptide synthesis.

The reaction container for solid phase peptide synthesis is preferably equipped with a column-shaped container and a centrifugal stirrer having no impeller (for example, see FIG. 1). The column-shaped container may have a bottom face and a lateral face each made from plastic or glass. The column-shaped container may or may not have a plastic or glass cover on the top. As long as solid phase peptide synthesis can be performed in the container, the centrifugal stirrer having no impeller may be placed at any position in the column-shaped container but is preferably placed at the lower center of the column-shaped container. A reactant, a reaction solution, and/or a washing solution can be placed from the top of the column-shaped container.

The reaction container for solid phase peptide synthesis is preferably equipped with a heating medium jacket (cover), a heating medium inlet port, and a heating medium outlet port on the outer side of the column-shaped container (for example, see FIG. 1). For example, a circulating water at about 5 to 80° C. may be introduced from the heating medium inlet port into the heating medium jacket, and the circulating water through the circulating water jacket may be discharged from the heating medium outlet port.

The reaction container for solid phase peptide synthesis is preferably, further equipped with a glass filter. The glass filter may be a crucible type, a Buchner funnel type, or a plate type, and, for example, a commercial product is available. The plate size of the glass filter is not limited to particular sizes and can be appropriately changed. The pore size of the glass filter can be smaller than the size of a resin (solid phase support) used for solid phase synthesis so as to filter a liquid while the resin is held on the filter. The glass filter is preferably located higher than the bottom face of the reaction container for solid phase peptide synthesis and/or lower than the centrifugal stirrer having no impeller (for example, see FIG. 1). When the glass filter is installed, a resin can be simply rapidly separated from a liquid such as a reaction solution and a washing solution, and this can improve the operation efficiency of the solid phase peptide synthesis.

The reaction container for solid phase peptide synthesis is preferably equipped with a cock, and, for example, a commercial product is available. The cock is preferably located lower than the bottom face of the reaction container for solid phase peptide synthesis and the glass filter (for example, see FIG. 1). When the cock is installed, an intended amount of the liquid in the reaction container for solid phase peptide synthesis can be discharged at any time, and this can simplify the separation operation of a resin from a liquid such as a reaction solution or a washing solution.

The reaction container for solid phase peptide synthesis is more preferably equipped with the glass filter and the cock.

The dimensions and the centrifugal force of the rotor of the centrifugal stirrer are not limited to particular values and can be appropriately changed.

The centrifugal stirrer preferably has a plurality of (for example, 2 to 10) outlet ports on the circumference. The discharge factor (total opening area of outlet ports×circumferential length) as an index of the stirring performance of a rotor is preferably 60 $cm^3$ to 6,000 $cm^3$ and more preferably 200 $cm^3$ to 2,000 $cm^3$.

Peptide

The peptide may be, for example, a peptide having an amino acid residue number of 5 to 150, a peptide having an amino acid residue number of 5 to 34, a peptide having an amino acid residue number of 15 to 100, a peptide having an amino acid residue number of 10 to 80, a peptide having an amino acid residue number of 15 to 80, a peptide having an amino acid residue number of 10 to 60, or a peptide having an amino acid residue number of 15 to 60.

The peptide may be, for example, abarelix, insulin and analogs thereof, endothelin, β-endorphin, oxytocin, calcitonin, carperitide, glucagon, glucagon-like peptide-1 (GLP-1), glucagon-like peptide-2 (GLP-2), ghrelin, goserelin, cholecystokinin, sinapultide, atrial natriuretic peptide (ANP), secretin, cetrorelix, somatostatin, degarelix, desmopressin, teduglutide, teriparatide, brain natriuretic peptide (BNP), vasopressin, parathormone, bradykinin, peginesatide, lanreotide, β-lipotropin, γ-lipotropin, leuprorelin, linaclotide, liraglutide, or a salt thereof. The salt is not specifically limited as long as it is a pharmaceutically acceptable salt. Examples of the salt include pharmaceutically acceptable acid addition salts, metal salts, ammonium salts, and organic amine addition salts. Examples of the acid addition salt include inorganic acid salts such as hydrochloride, nitrate, sulfate, and phosphate; and organic acid salts such as oxalate, acetate, trifluoroacetate, maleate, fumarate, tartrate, citrate, lactate, malate, succinate, gluconate, ascorbate, and p-toluenesulfonate. Examples of the metal salt include alkali metal salts such as a sodium salt and a potassium salt; alkaline earth metal salts such as a magnesium salt and a calcium salt; and an aluminum salt and a zinc salt. Examples of the ammonium salt include an ammonium salt and a tetramethylammonium salt. Examples of the organic amine addition salt include a piperidine addition salt. Specifically, an acid addition salt, an organic acid salt, and the like are preferred, and acetate is more preferred.

Solid Phase Synthesis

The process conditions for the solid phase synthesis have been well established, and therefore any known method (for example, Merrifield solid phase synthesis) can be used without particular limitation as long as a centrifugal stirrer having no impeller is used as the stirrer. The reaction in the solid phase synthesis includes protecting group introduction reaction before coupling reaction, activation reaction of a carboxyl group or an amino group contributing to coupling reaction of a peptide before coupling reaction, coupling reaction, resin cleavage reaction, and deprotection reaction after coupling reaction and resin cleavage reaction. For the deprotection of Fmoc group (9-fluorenylmethyloxycarbonyl group), DMF/20% piperidine may be used. For the deprotection of Boc group (tert-butoxycarbonyl group), trifluoroacetic acid may be used. Ninhydrin reaction by Kaiser Test or another method may be used to detect the presence of unreacted amino groups.

See Examples below for examples of the solid phase synthesis.

Effect

According to the peptide production method of the present invention, for example, a large amount of a peptide can be synthesized. The amount of a peptide to be synthesized is preferably larger than the amount of a peptide synthesized by a peptide production method without the centrifugal stirrer having no impeller. For example, the amount may be 1 g or more, 10 g or more, 100 g or more, 200 g or more, or 300 g or more.

The peptide synthesized by the peptide production method of the present invention preferably has a higher purity than that of a peptide synthesized by a peptide production method without the centrifugal stirrer having no impeller. The HPLC purity is preferably, for example, 60% or more, 70% or more, 80% or more, or 90% or more.

The peptide synthesized by the peptide production method of the present invention preferably contains a smaller amount of reaction by-products including de-tritylated products than a peptide synthesized by a peptide production method without the centrifugal stirrer having no impeller. The content of de-tritylated products is preferably, for example, 5% or less, 3% or less, or 1% or less.

The present invention encompasses embodiments of various combinations of the above constitutions within the technical scope of the present invention as long as the advantageous effects of the invention are exerted.

EXAMPLES

The present invention will next be described more specifically with reference to examples, but the present invention is not intended to be limited to these examples, and many modifications can be made by a person skilled in the art within the technical idea of the present invention.

In the examples, the following HPLC conditions were used for measurement.

Column: Waters XBridge Shield 18, 3.5 μm, 4.6×150 mm
Mobile phase A: 0.1% aqueous TFA
Mobile phase B: 0.08% TFA in acetonitrile
Flow rate: 1 mL/min
Detector: UV 220 nm

TABLE 1

Gradient program A

| | Time (min) | | | | |
|---|---|---|---|---|---|
| | 0.00 | 10.00 | 40.00 | 40.10 | 50.00 |
| Mobile phase A (%) | 30 | 30 | 0 | 30 | 30 |
| Mobile phase B (%) | 70 | 70 | 100 | 70 | 70 |

TABLE 2

Gradient program B

| | Time (min) | | | | |
|---|---|---|---|---|---|
| | 0.00 | 10.00 | 40.00 | 40.10 | 50.00 |
| Mobile phase A (%) | 40 | 40 | 0 | 40 | 40 |
| Mobile phase B (%) | 60 | 60 | 100 | 60 | 60 |

TABLE 3

Gradient program C

| | Time (min) | | | | |
|---|---|---|---|---|---|
| | 0.00 | 10.00 | 40.00 | 40.10 | 50.00 |
| Mobile phase A (%) | 85 | 85 | 50 | 85 | 85 |
| Mobile phase B (%) | 15 | 15 | 50 | 15 | 15 |

TABLE 4

Gradient program D

| | Time (min) | | | | |
|---|---|---|---|---|---|
| | 0.00 | 10.00 | 40.00 | 40.10 | 50.00 |
| Mobile phase A (%) | 20 | 20 | 0 | 20 | 20 |
| Mobile phase B (%) | 80 | 80 | 100 | 80 | 80 |

In the disclosure, pseudo-pro represents pseudoproline, Trt represents trityl group, HOBt represents 1-hydroxy-1H-benzotriazole monohydrate, DMF represents N,N-dimethylformamide, DIC represents diisopropylcarbodiimide, DIEA represents diisopropylethylamine, Oxyma represents ethyl (hydroxyimino)cyanoacetate, TFA represents trifluoroacetic acid, TIS represents tri(isopropyl)silane, EDT represents ethanedithiol, Cleavage mixture represents acetic acid/trifluoroethanol/dichloromethane (volume ratio: 10/10/80), IPE represents isopropyl ether, and TFE represents 2,2,2-trifluoroethanol.

Solid Phase Synthesis of 34-Residue Peptide

Experimental Example 1

Synthesis of A-Fragment-Resin (Boc-Ser(tBu)-Val-Ser(Pseudo-pro)-Glu(tBu)-Ile-Gln(Trt)-Leu-Met-His(Trt)-Asn(Trt)-Leu-Gly-O-Trt(2-Cl)-Resin) (Side Chain-Protected AFR-Resin) (Using an M-Revo (Registered Trademark))

1. Coupling Reaction
(1) In a reaction container, H-Gly-O-Trt(2-Cl)-resin (80.00 g), Fmoc (9-fluorenylmethoxycarbonyl)-amino acid (2.5 eq.), HOBt as an activator (22.42 g, 2.5 eq.), DMF as a reaction solvent (800 mL), and DIC (25.70 mL) were placed.
(2) The mixture was centrifugal-stirred using an M-Revo (registered trademark) for 2 hours or more.
(3) The reaction solvent was removed, and the Fmoc-amino acid-introduced resin was washed with DMF (800 mL), dichloromethane (800 mL), and DMF (800 mL) using the M-Revo (registered trademark).
(4) A small amount of the Fmoc-amino acid-introduced resin was sampled and was subjected to Kaiser Test, and no coloration of the resin was ascertained. If resin beads were colored by Kaiser Test, the operations (1) to (3) were repeated until the resin beads were not colored.
2. Deprotection of Fmoc Group
(5) To the resulting Fmoc-amino acid-introduced resin, 20% piperidine/DMF (800 mL) was added.
(6) The mixture was centrifugal-stirred using the M-Revo (registered trademark) for 20 minutes or more.
(7) The reaction solvent was removed, and the residue was washed with DMF (800 mL), dichloromethane (800 mL), and DMF (800 mL) using the M-Revo (registered trademark).
(8) Kaiser Test was performed to ascertain coloration of the resin beads.
(9) The operations (1) to (8) were performed until the following side chain-protected AFR-resin (230 g) was obtained. The serine (pseudoproline) residue was introduced as Fmoc-valine-serine (pseudoproline) that was a dipeptide with an N-terminus protected by an Fmoc group.

[Chemical Formula 1]

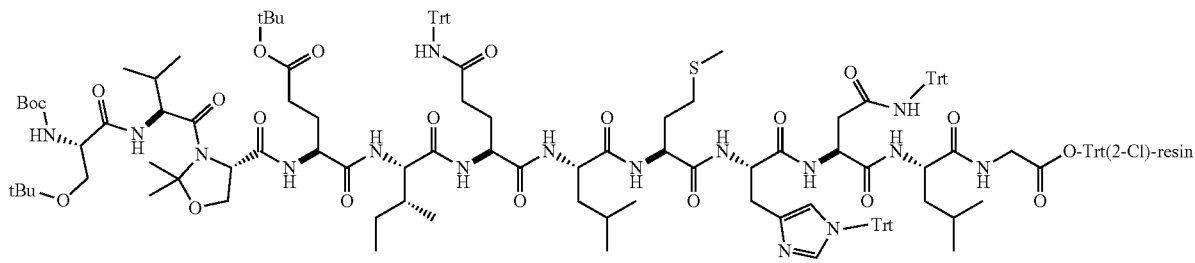

Experimental Example 2

Synthesis of B-Fragment-Resin (H-Lys(Boc)-His(Trt)-Leu-Asn(Trt)-Ser(tBu)-Met-Glu(tBu)-Arg(Pbf)-Val-Glu(tBu)-Trp(Boc)-Leu-Arg(Pbf)-Lys(Boc)-Lys(Boc)-Leu-Gln(Trt)-Asp(tBu)-Val-His(Trt)-Asn(Trt)-Phe-O-Trt(2-Cl)-Resin) (Side Chain-Protected BFR-Resin) (Using an M-Revo (Registered Trademark))

1. Introduction of Fmoc-Amino Acid to Resin (1) In a reaction container, Cl-Trt(2-Cl)-resin (40.00 g) and Fmoc-Phe-OH (56.17 g) were placed under an argon gas atmosphere.

(2) Dichloroethane (400 mL) and DIEA (25.25 mL) were added.

(3) The mixture was centrifugal-stirred using an M-Revo (registered trademark) for 3 hours or more.

(4) The reaction solvent was removed, and DIEA (5.05 mL), methanol (40 mL), and dichloroethane in such a volume as to enable stirring were added.

(5) The mixture was centrifugal-stirred for 1 hour using the M-Revo (registered trademark) under an argon gas atmosphere.

(6) The reaction solvent was removed, and the residue was washed with DMF (400 mL), dichloromethane (400 mL), and DMF (400 mL) using the M-Revo (registered trademark).

(7) A small amount of the Fmoc-Phe-O-Trt(2-Cl)-resin was sampled and subjected to Kaiser Test, and no coloration of the resin beads was detected.

2. Deprotection of Fmoc Group (8) To the resulting Fmoc-Phe-O-Trt(2-Cl)-resin, 20% piperidine/DMF (400 mL) was added.

(9) The mixture was centrifugal-stirred using the M-Revo (registered trademark) for 20 minutes or more.

(10) The reaction solvent was removed, and the residue was washed with DMF (400 mL), dichloromethane (400 mL), and DMF (400 mL) using the M-Revo (registered trademark).

(11) Kaiser Test was performed to ascertain coloration of the resin beads.

(12) An H-Phe-O-Trt(2-Cl)-resin was obtained.

3. Coupling Reaction

(13) In a reaction container, the H-Phe-O-Trt(2-Cl)-resin obtained in (12), Fmoc-amino acid (2.5 eq.), HOBt (19.59 g, 2.5 eq.), DMF (10 to 20 v/w), and DIC (22.45 mL, 2.5 eq.) were placed.

(14) The mixture was centrifugal-stirred using an M-Revo (registered trademark) for 2 hours or more.

(15) The reaction solvent was removed, and the Fmoc-amino acid-introduced resin was washed with DMF, dichloromethane, and DMF using the M-Revo (registered trademark).

(16) A small amount of the Fmoc-amino acid-introduced resin was sampled and subjected to Kaiser Test, and no coloration of the resin beads was detected. If resin beads were colored by Kaiser Test, the operations (13) to (15) were repeated until the resin beads were not colored by Kaiser Test.

4. Deprotection of Fmoc Group

(17) To the resulting Fmoc-amino acid-introduced resin, 20% piperidine/DMF (400 mL) was added.

(18) The mixture was centrifugal-stirred using the M-Revo (registered trademark) for 20 minutes or more.

(19) The reaction solvent was removed, and the residue was washed with DMF (400 mL), dichloromethane (400 mL), and DMF (400 mL) using the M-Revo (registered trademark).

(20) Kaiser Test was performed to ascertain coloration of the resin beads.

(21) The operations (13) to (20) were performed until the following side chain-protected BFR-resin (310 g) was obtained.

[Chemical Formula 2]
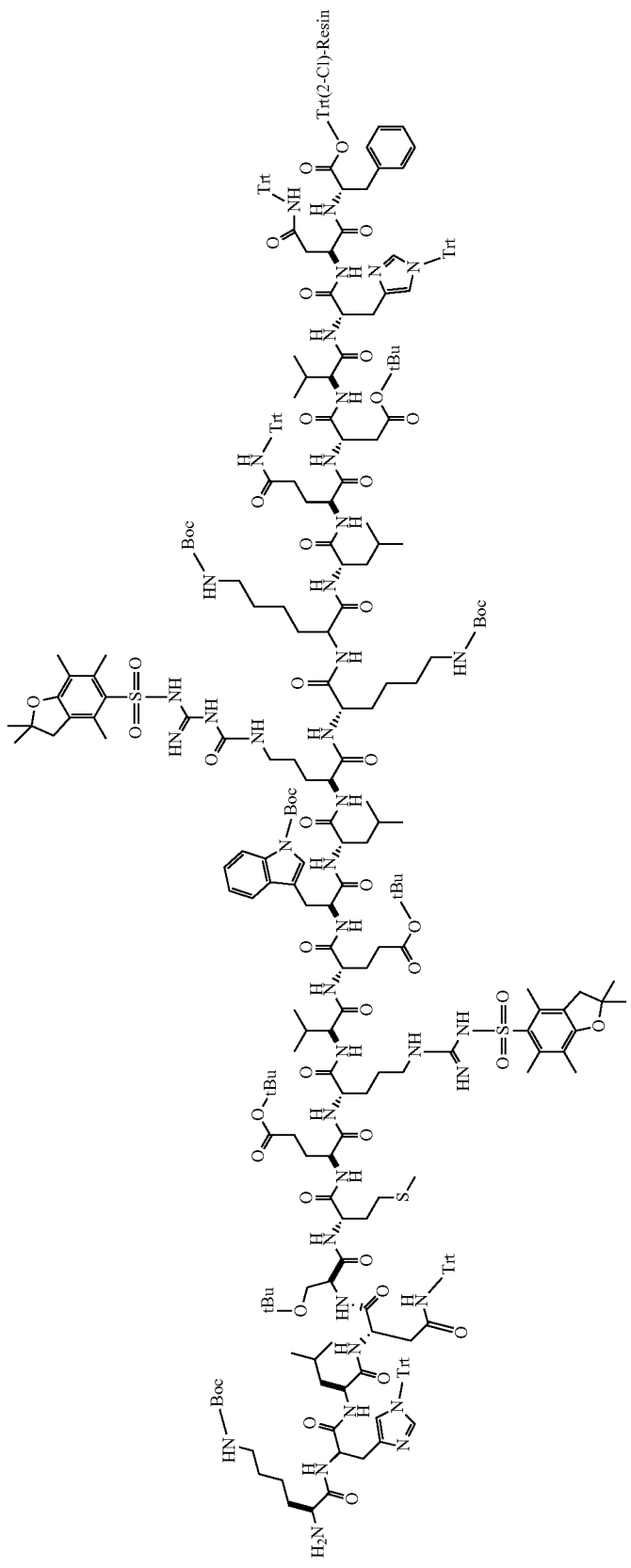

Experimental Example 3

Cleavage of Protected Peptide from Side Chain-Protected BFR-Resin (Using an M-Revo (Registered Trademark))

(1) Into a container containing the side chain-protected BFR-resin (80 g), a degassed Cleavage mixture (800 mL) was added.
(2) The mixture was centrifugal-stirred using an M-Revo (registered trademark) for 2 hours.
(3) The reaction solution was filtered and was washed with Cleavage mixture (80 mL) three times and then with dichloromethane (160 mL).
(4) The filtrate was concentrated under reduced pressure at an outside temperature of 25° C.
(5) To the residue after concentration, dichloromethane (160 mL) was added to dissolve crystals.
(6) In a reaction container, IPE (4000 mL) was placed, and the solution resulting from (5) was added dropwise.
(7) The mixture was stirred at room temperature for 1 hour, and then crystals were filtered under reduced pressure and washed with IPE (800 mL).
(8) The product was dried under vacuum at room temperature, giving side chain-protected B-fragment (67.95 g).

[Chemical Formula 3]

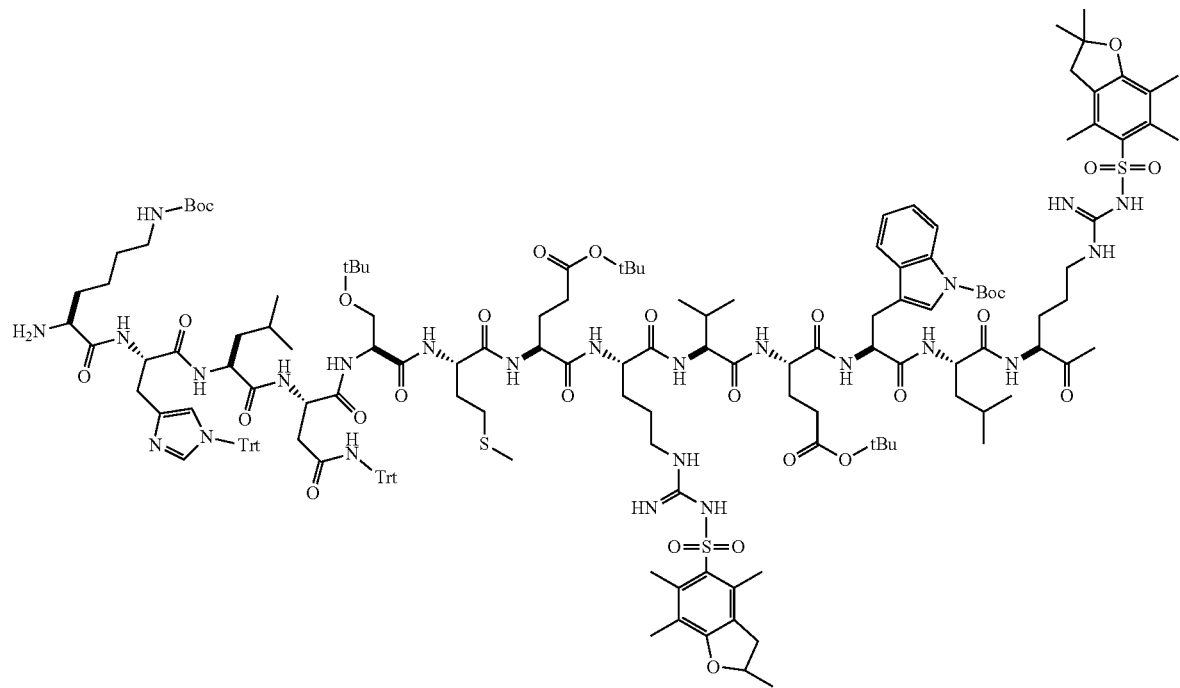

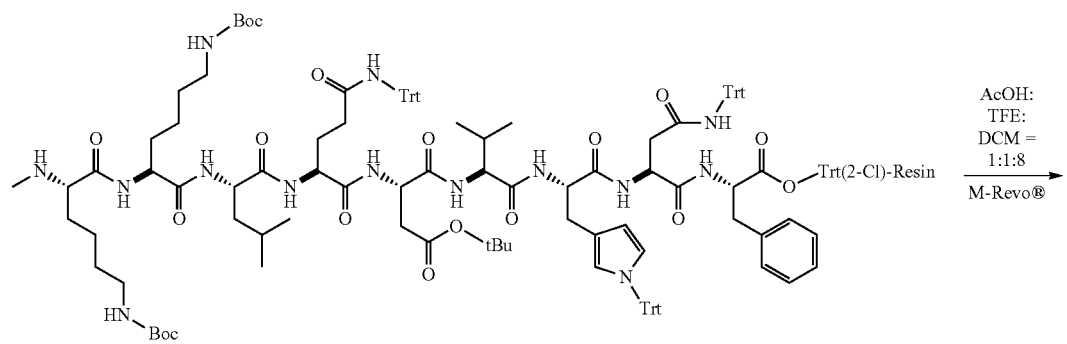

-continued

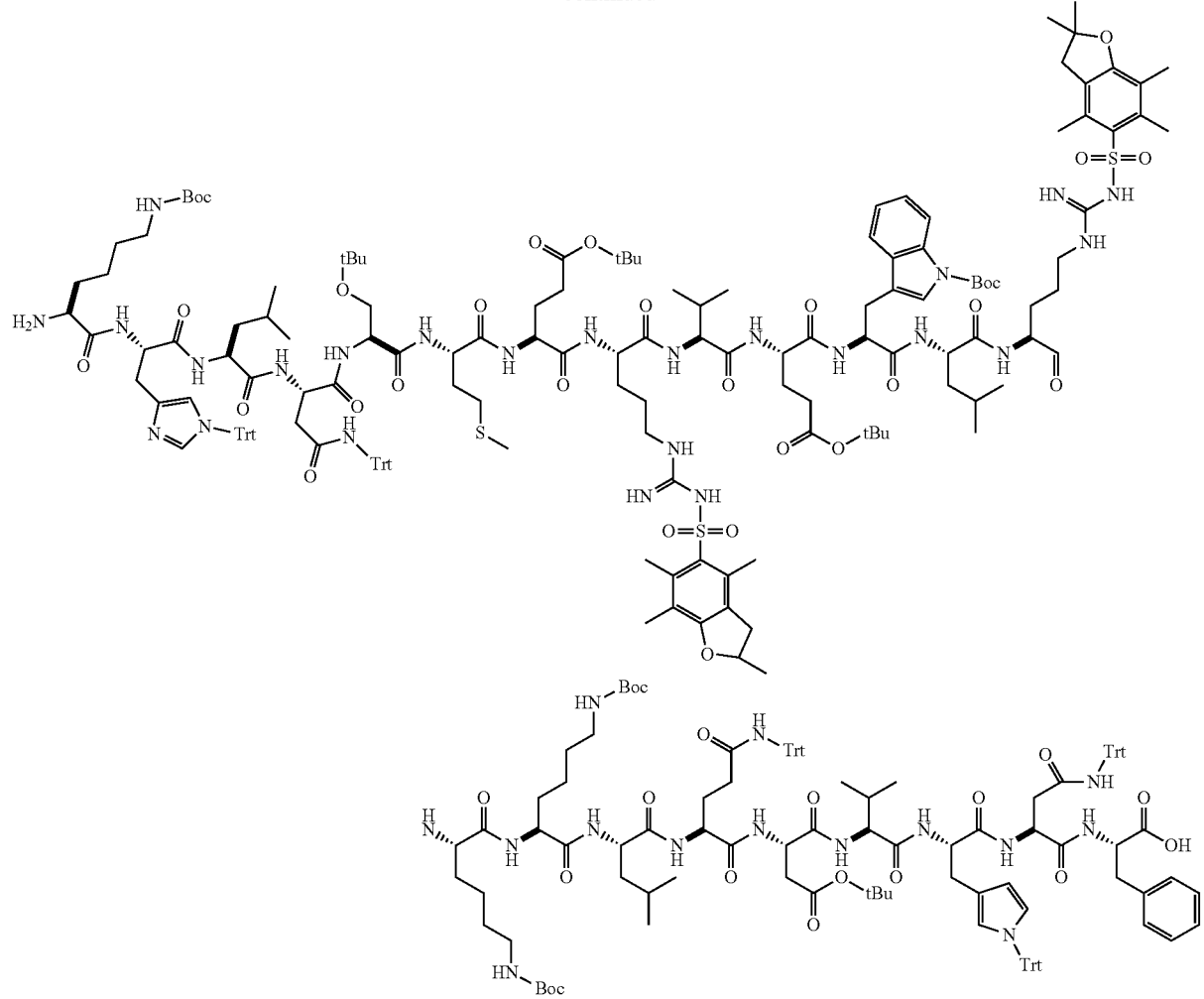

Comparative Examples 1 and 2

The same solid phase synthesis as in Experimental Example 3 was performed except that a stirrer was used in place of the M-Revo (registered trademark), giving side chain-protected B-fragment.

HPLC Analysis (Comparative Examples 1 and 2 and Experimental Example 3)

Figure 8:
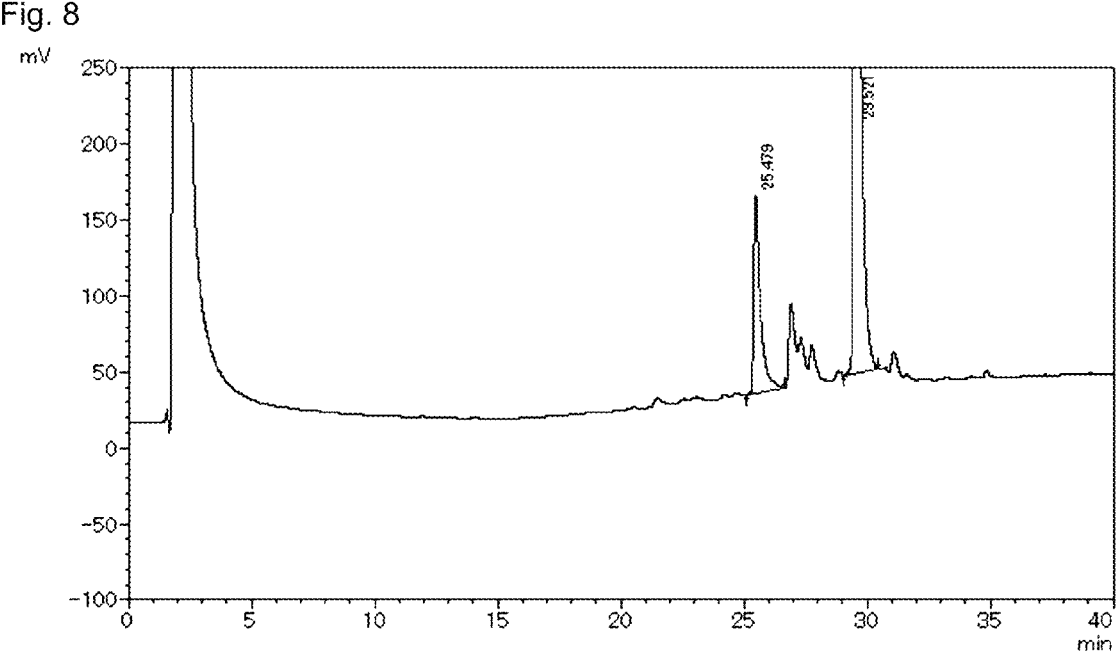
FIG. 8 is an HPLC chromatogram of a product in Comparative Example 1.
Figure 9:
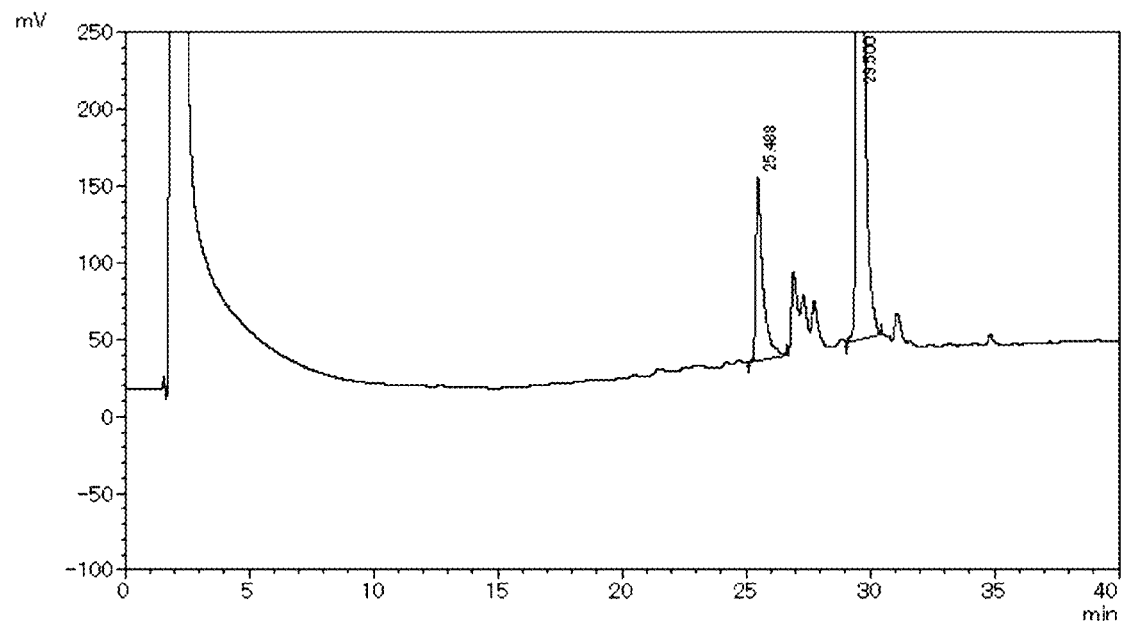
FIG. 9 is an HPLC chromatogram of a product in Comparative Example 2.
Figure 10:
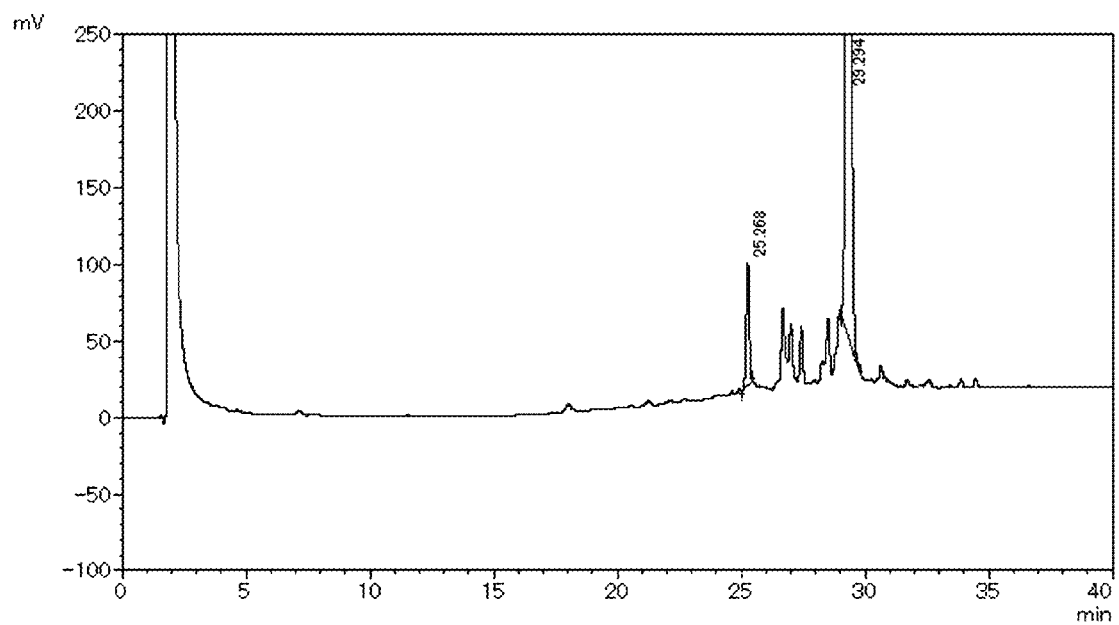
FIG. 10 is an HPLC chromatogram of a product in Experimental Example 3.

Acetonitrile solutions of the products of Comparative Examples 1 and 2 and Experimental Example 3 were subjected to HPLC analysis, and the results are shown in Tables 5 to 7 and FIGS. 8 to 10. Tables 5, 6, and 7 show retention times and contents of products (de-tritylated by-product and B-fragment) in the acetonitrile solutions of the products of Comparative Example 1, Comparative Example 2, and Experimental Example 3, respectively, by HPLC analysis. FIGS. 8, 9, and 10 show HPLC chromatograms (gradient program A) of the acetonitrile solutions of the products of Comparative Example 1, Comparative Example 2, and Experimental Example 3, respectively.

TABLE 5

| Peak | Retention Time (min) | Area % |
|---|---|---|
| de-Tritylated By-product | 25.48 | 12.826 |
| B-fragment | 29.52 | 70.475 |

TABLE 6

| Peak | Retention Time (min) | Area % |
|---|---|---|
| de-Tritylated By-product | 25.49 | 10.867 |
| B-fragment | 29.50 | 72.412 |

TABLE 7

| Peak | Retention Time (min) | Area % |
|---|---|---|
| de-Tritylated By-product | 25.27 | 4.786 |
| B-fragment | 29.29 | 69.157 |

The results of Experimental Example 3 and Comparative Examples 1 and 2 are shown in Table 8.

TABLE 8

| Experimental Example | Stirring method | HPLC purity (Area %) | |
| --- | --- | --- | --- |
| | | B-fragment | De-tritylated by-product |
| Experimental Example 3 | M-Revo | 69.2 | 4.8 |
| Comparative Example 1 | Stirrer | 70.5 | 12.8 |
| Comparative Example 2 | Stirrer | 72.4 | 10.9 |

The above results reveal that the B-fragment in Experimental Example 3 had an HPLC purity of 69.2%, which was substantially equivalent to those in Comparative Examples 1 and 2, but the content of the de-tritylated by-product was 4.79%, which was not higher than a half of those in Comparative Examples 1 and 2. In other words, the solid phase synthesis using the M-Revo (registered trademark) enabled the production of the B-fragment having a higher purity or containing a smaller amount of the unfavorable de-tritylated product than the solid phase synthesis using a stirrer.

Experimental Example 4

Production of 34-Residue Peptide

The side chain-protected AFR-resin prepared in Experimental Example 1 was treated in the same manner as in Experimental Example 3 to cleave the side chain-protected A-fragment from the resin, then the C-terminal carboxyl group thereof was activated, and the side chain-protected B-fragment was reacted to synthesize side chain-protected 34-residue peptide. The side chain protecting groups were deprotected to give an intended peptide.

Experimental Example 5

Synthesis of Side Chain-Protected A-Fragment-Resin (Boc-Ser(tBu)-Val-Ser(pseudo-pro)-Glu(tBu)-Ile-Gln(Trt)-Leu-Met-His(Trt)-Asn(Trt)-Leu-Gly-O-Trt(2-Cl)-Resin) (Side Chain-Protected AFR-Resin) (Using an M-Revo (Registered Trademark))

1. Introduction of Fmoc-Amino Acid to Resin (1) In a recovery flask, Fmoc-Leu-OH (2.5 eq.), DMF, HOBt (2.5 eq.), and DIC (2.5 eq.) were placed and stirred for 30 minutes. Into a reaction container containing H-Gly-O-Trt(2-Cl)-resin (80.00 g), the reaction solution in the recovery flask was added, and the whole was stirred using an M-Revo (registered trademark) for 2 hours or more. The reaction solvent was removed, and the resin was washed with DMF, dichloromethane, and DMF, giving Fmoc-Leu-Gly-O-Trt(2-Cl)-resin.

2. Deprotection of Fmoc Group (2) To the Fmoc-Leu-Gly-O-Trt(2-Cl)-resin, a 20% piperidine/DMF solution (10 v/w) was added. The mixture was stirred using an M-Revo for 20 minutes, and then the reaction solvent was removed. The residue was washed with DMF (10 v/w, 5 times), dichloromethane (10 v/w, 5 times), and DMF (10 v/w, 5 times), giving H-Leu-Gly-O-Trt(2-Cl)-resin.

3. Coupling Reaction (3) To the H-Leu-Gly-O-Trt(2-Cl)-resin, Fmoc-Asn(Trt)-OH (2.5 eq.), HOBt (2.5 eq.), DIC (2.5 eq.), and DMF in such a volume as to enable stirring (about 10 v/w) were added. The mixture was stirred using the M-Revo (registered trademark) for 2 hours or more, and then the reaction solvent was removed. The residue was washed with DMF, dichloromethane, and DMF, giving Fmoc-Asn(Trt)-Leu-Gly-O-Trt(2-Cl)-resin.

(4) To the Fmoc-Asn(Trt)-Leu-Gly-O-Trt(2-Cl)-resin, a 20% piperidine/DMF solution (10 v/w) was added. The mixture was stirred using the M-Revo (registered trademark) for 20 minutes, and then the reaction solvent was removed. The residue was washed with DMF, dichloromethane, and DMF, giving H-Asn(Trt)-Leu-Gly-O-Trt(2-Cl)-resin.

(5) Subsequently, the operations (1) and (2) were repeated for introduction of Fmoc-amino acids and deprotection of Fmoc group. After the introduction of Fmoc-Met-OH, argon bubbling was performed for 10 minutes or more before the start of stirring.

(6) Boc-Ser(tBu)-OH (2.5 eq.) as the 12th residue was coupled in the same manner as in (2), and then the reaction solvent was removed. The residue was washed with MeOH and then dried under reduced pressure, giving side chain-protected AFR-resin (144.12 g).

4. Cleavage of Protected Peptide from Resin and Purity Measurement (7) To a sample (about 20 to 50 mg) of the side chain-protected AFR-resin prepared in (6), acetic acid/dichloromethane (acetic acid/dichloromethane=1/9 in terms of volume) was added, and the whole was stirred for 1 to 2 hours. The reaction solution was diluted with acetonitrile and was analyzed by HPLC.

Figure 11:
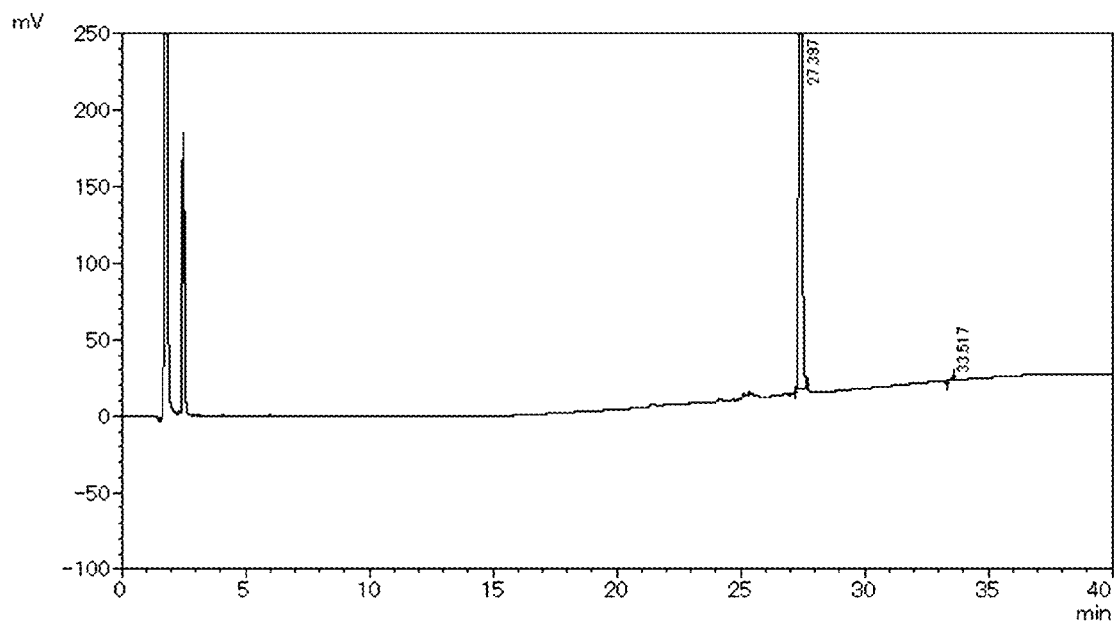
FIG. 11 is an HPLC chromatogram of an acetonitrile solution of a product in Experimental Example 5.

The results reveal that the target A-fragment has a purity of 94.1% ($t_R$=27.4), whereas the content of the de-tritylated by-product was 0.55% ($t_R$=21.5) (see FIG. 11 and Table 9, gradient program B).

TABLE 9

| Peak | Retention Time (min) | Area % |
| --- | --- | --- |
| de-Tritylated By-product | 21.50 | 0.545 |
| A-fragment | 27.40 | 94.072 |

Comparative Example 3

Preparation of Side Chain-Protected A-Fragment-Resin (Boc-Ser(tBu)-Val-Ser(pseudo-pro)-Glu(tBu)-Ile-Gln(Trt)-Leu-Met-His(Trt)-Asn(Trt)-Leu-Gly-O-Trt(2-Cl)-Resin) (Side Chain-Protected AFR-Resin) (Using a Fully Automated Microwave Peptide Synthesizer (Initiator+ Alstra Manufactured by Biotage Japan))

1. Introduction of Fmoc-Amino Acid to Resin (1) In a reaction container, H-Gly-O-Trt(2-Cl)-resin (122 mg) and DMF (4.5 mL) were placed, and the resin was allowed to swell for 20 minutes. After filtration, a 0.5M DMF solution of Fmoc-Leu-OH (0.8 mL, 0.4 mmol, 4 eq.), a 0.5M DMF solution of DIC (0.8 mL), and a 0.2M DMF solution of HOBt (2.0 mL) were added. The mixture was reacted by microwave (MW) irradiation at 75° C. for 5 minutes, and then the reaction solvent was removed. The residue was washed with DMF (18 mL), giving Fmoc-Leu-Gly-O-Trt(2-Cl)-resin.

2. Deprotection of Fmoc Group (2) To the Fmoc-Leu-Gly-O-Trt(2-Cl)-resin, a 20% piperidine/DMF solution (4.5 mL) was added. After stirring for 3 minutes, the reaction solvent was removed, and a 20% piperidine/DMF solution (4.5 mL) was added. After stirring for 10 minutes, the reaction solvent was removed. The residue was washed with DMF (18 mL), giving H-Leu-Gly-O-Trt(2-Cl)-resin.

3. Coupling Reaction (3) To the H-Leu-Gly-O-Trt(2-Cl)-resin, a 0.5M DMF solution of Fmoc-Asn(Trt)-OH (0.8 mL), a 0.5M DMF solution of DIC (0.8 mL), and a 0.2M DMF solution of HOBt (2.0 mL) were added. The mixture was reacted by MW irradiation at 75° C. for 5 minutes, and then the reaction solvent was removed. The residue was washed with DMF (18 mL), giving Fmoc-Asn(Trt)-Leu-Gly-O-Trt(2-Cl)-resin.

(4) Subsequently, the deprotection and the Fmoc amino acid-coupling were repeated in the same manner as in (2) and (3) (the coupling reaction of Fmoc-His(Trt)-OH was performed at 50° C. for 10 minutes). Boc-Ser(tBu)-OH (4.0 eq.) as the last 12th residue was coupled in the same manner as in (1), and then the reaction solvent was removed. The residue was washed with MeOH (13.5 mL) and was dried under reduced pressure, giving side chain-protected AFR-resin (350 mg).

Figure 12:
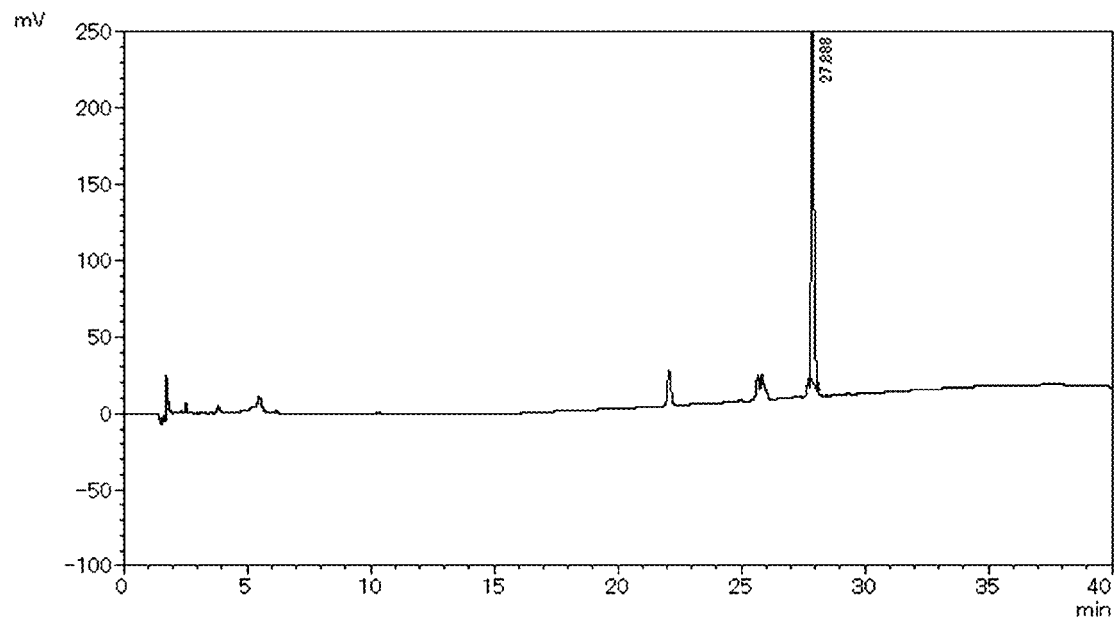
FIG. 12 is an HPLC chromatogram of a product in Comparative Example 3.

4. Cleavage of Protected Peptide from Resin and Purity Measurement (5) To a sample (about 20 to 50 mg) of the side chain-protected AFR-resin, acetic acid/TFE/dichloromethane (acetic acid/TFE/dichloromethane=1/1/9 in terms of volume) was added, and the whole was stirred for 2 hours. The reaction solution was diluted with acetonitrile and was analyzed by HPLC. The results reveal that the target A-fragment has a purity of 66.1% ($t_R$=27.9), whereas the content of the de-tritylated by-product was 7.5% ($t_R$=22.1) (see FIG. 12 and Table 10, gradient program B).

TABLE 10

| Peak | Retention Time (min) | Area % |
| --- | --- | --- |
| de-Tritylated By-product | 22.09 | 7.547 |
| A-fragment | 27.89 | 66.111 |

Experimental Example 6

Synthesis of 15-Residue Peptide-Resin (H-Arg (Pbf)-Val-Glu(tBu)-Trp(Boc)-Leu-Arg(Pbf)-Lys (Boc)-Lys(Boc)-Leu-Gln(Trt)-Asp(tBu)-Val-His (Trt)-Asn(Trt)-Phe-O-Trt(2-Cl)-Resin) (the 1st to 4th Residues were Introduced by Stirring with a Shaker (a High Speed Mixer (Cute Mixer) CM-1000 Manufactured by EYELA or a High Speed Mixer ASCM-1 Manufactured by As One); then for the Introduction of the 5th and Subsequent Residues, the Peptide Intermediate Resin was Divided into Two Portions; One Portion was Subjected to Synthesis by Stirring with an M-Revo (Registered Trademark); and the Other was Subjected to Synthesis by Stirring with the Shaker)

1. Introduction of Fmoc-Amino Acid to Resin (1) Under an argon atmosphere, Cl-Trt(2-Cl)-resin (4.00 g), Fmoc-Phe-OH (6.32 g), DIEA (2.79 mL), and dichloroethane (28.0 mL) were placed in a reaction container. The mixture was stirred at room temperature for 3.5 hours and was washed with dichloroethane (28.0 mL) for 5 times.

(2) To the washed resin, MeOH (4.00 mL), DIEA (0.8 mL), and dichloroethane (28.0 mL) were added. After stirring for 20 minutes, the reaction solvent was removed. The residue was washed with DMF, dichloromethane, and DMF, giving Fmoc-Phe-O-Trt(2-Cl)-resin.

2. Deprotection of Fmoc Group (3) To the Fmoc-Phe-O-Trt(2-Cl)-resin, a 20% piperidine/DMF solution (40.0 mL, 10 v/w) was added, then the whole was stirred for 20 minutes, and the reaction solvent was removed. The residue was washed with DMF (28.0 mL, 7 v/w, 5 times), dichloromethane (28.0 mL, 7 v/w, 5 times), and DMF (28.0 mL, 7 v/w, 5 times), giving H-Phe-O-Trt (2-Cl)-resin.

3. Coupling Reaction (4) In a flask, Fmoc-Asn(Trt)-OH (9.73 g, 16.3 mmol), HOBt (2.20 g), DIC (2.52 mL), and DMF (40.0 mL) were placed and stirred for 30 minutes. The solution was added to the H-Phe-O-Trt(2-Cl)-resin, then the flask was rinsed with DMF, and the DMF was added. The whole was stirred for 2 hours, and then the reaction solvent was removed.

(5) The resin was washed with DMF, giving Fmoc-Asn (Trt)-Phe-O-Trt(2-Cl)-resin.

4. Deprotection of Fmoc Group (6) To the Fmoc-Asn(Trt)-Phe-O-Trt(2-Cl)-resin, a 20% piperidine/DMF solution (40.0 mL) was added, then the whole was stirred for 20 minutes, and the reaction solvent was removed. The residue was washed with DMF, dichloromethane, and DMF, giving H-Asn(Trt)-Phe-O-Trt(2-Cl)-resin.

5. Coupling Reaction (7) To the H-Asn(Trt)-Phe-O-Trt(2-Cl)-resin, Fmoc-His (Trt)-OH (1.01 g), HOBt (2.20 g), DIC (2.52 mL), and DMF (in such a volume as to enable stirring) were added, then the mixture was stirred for 2 hours or more, and the reaction solvent was removed.

(8) The resin was washed with DMF, dichloromethane, and DMF, giving Fmoc-His(Trt)-Asn(Trt)-Phe-O-Trt(2-Cl)-resin.

(9) Subsequently, the deprotection and the coupling were repeated in the same manner as in (4) and (5).

(10) After coupling of Fmoc-Arg(Pbf)-OH as the 15th residue, the Fmoc group was deprotected in the same manner as in (3), and the resin was washed with dichloromethane and MeOH and dried under reduced pressure, giving 15-residue peptide-resin (10.7 g).

6. Cleavage of Protected Peptide from Resin and Purity Measurement

Figure 13:
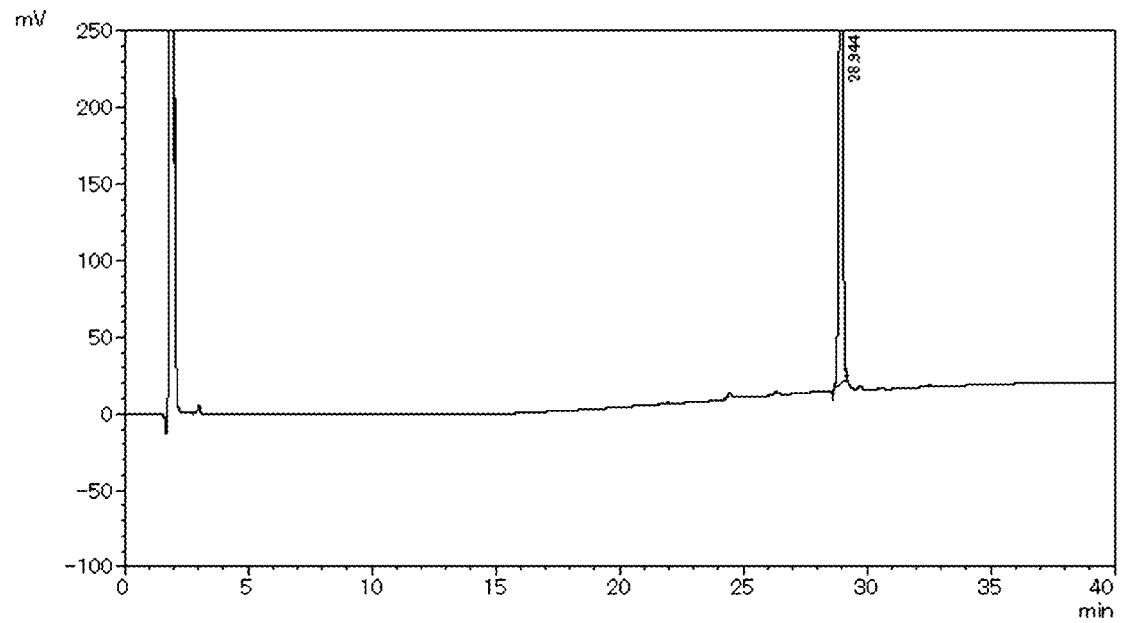
FIG. 13 is an HPLC chromatogram of a product in Experimental Example 6 (a product synthesized by using an M-Revo in coupling process for the 5th and subsequent residues).
Figure 14:
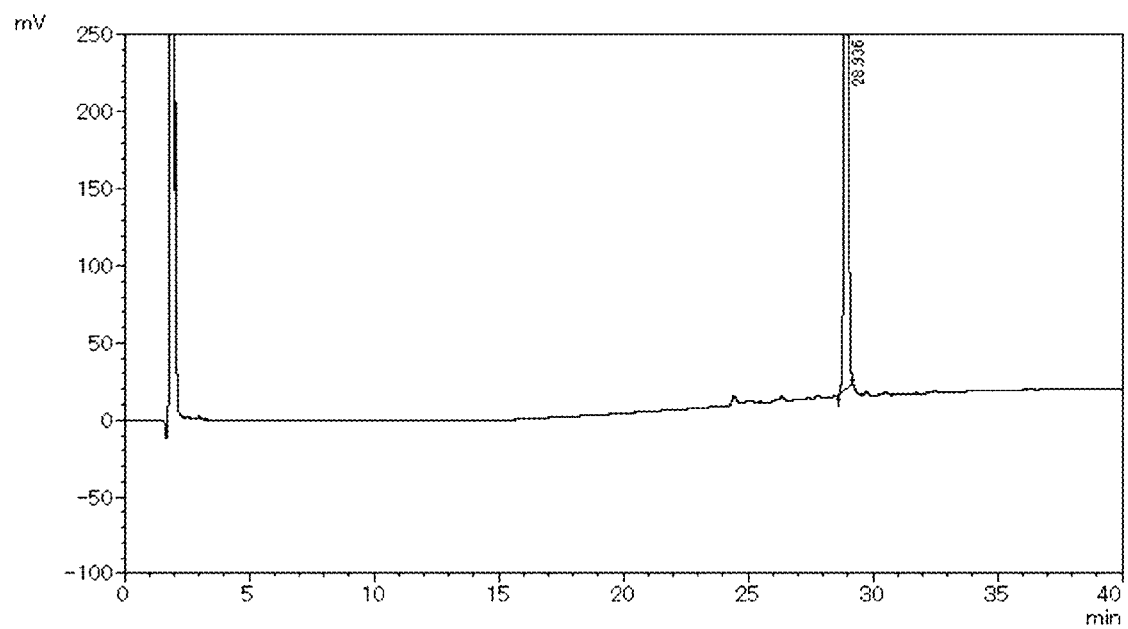
FIG. 14 is an HPLC chromatogram of a product in Experimental Example 6 (a product synthesized by using a shaker).

(11) To a sample (about 20 to 50 mg) of the 15-residue peptide-resin, acetic acid/dichloromethane (acetic acid/dichloromethane=1/1 in terms of volume) was added, and the mixture was stirred for 1 to 2 hours. The reaction solution was diluted with acetonitrile and was analyzed by HPLC. The results of the product synthesized by using an M-Revo (registered trademark) in a part of the process (coupling for the 5th and subsequent residues) are shown in Table 11 and FIG. 13 (gradient program A), and the results of the product synthesized by using a shaker are shown in Table 12 and FIG. 14 (gradient program A). The results reveal that the former exhibits a higher HPLC purity than the latter (the HPLC purity of the product synthesized by using an M-Revo (registered trademark) in the coupling process for the 5th and subsequent residues: 93.1%, the HPLC purity of the product synthesized by using a shaker: 89.4%).

TABLE 11

| Peak | Retention Time (min) | Area % |
| --- | --- | --- |
| 15-AA Peptide | 28.94 | 93.082 |

TABLE 12

| Peak | Retention Time (min) | Area % |
| --- | --- | --- |
| 15-AA Peptide | 28.94 | 89.371 |

TABLE 13

| Peak | Retention Time (min) | Area % |
| --- | --- | --- |
| 16-AA Peptide | 20.66 | 63.426 |

Experimental Example 7

Synthesis of 16-Residue Peptide-Resin (H-Glu(tBu)-Arg(Pbf)-Val-Glu(tBu)-Trp(Boc)-Leu-Arg(Pbf)-Lys(Boc)-Lys(Boc)-Leu-Gln(Trt)-Asp(tBu)-Val-His(Trt)-Asn(Trt)-Phe-O-Trt(2-Cl)-Rresin) (Using a Fully Automated Microwave Peptide Synthesizer (Initiator+ Alstra Manufactured by Biotage Japan))

1. Introduction of Fmoc-Amino Acid to Resin
(1) In a reaction container, H-Phe-O-Trt(2-Cl)-resin (179 mg) and DMF (4.5 mL) were placed, and the resin was allowed to swell for 20 minutes. After removal of the DMF, a 0.5M DMF solution of Fmoc-Asn(Trt)-OH (0.8 mL), a 0.2M DMF solution of DIC (2.0 mL), and a 0.5M DMF solution of Oxyma (0.8 mL) were added. The mixture was reacted by microwave (MW) irradiation at 75° C. for 5 minutes, and then the reaction solvent was removed. The residue was washed with DMF (18 mL), giving Fmoc-Asn(Trt)-Phe-O-Trt(2-Cl)-resin.

2. Deprotection of Fmoc Group
(2) To the Fmoc-Asn(Trt)-Phe-O-Trt(2-Cl)-resin, a 20% piperidine/DMF solution (4.5 mL) was added. After stirring for 3 minutes, the reaction solvent was removed, and a 20% piperidine/DMF solution (4.5 mL) was added. After stirring for 10 minutes, the reaction solvent was removed, and the residue was washed with DMF (18 mL), giving H-Asn(Trt)-Phe-O-Trt(2-Cl)-resin.

3. Coupling Reaction
(3) To the H-Asn(Trt)-Phe-O-Trt(2-Cl)-resin, a 0.5M DMF solution of Fmoc-His(Trt)-OH (0.8 mL), a 0.5M DMF solution of DIC (0.8 mL), and a 0.2M DMF solution of Oxyma (2.0 mL) were added.
(4) The mixture was reacted by MW irradiation at 50° C. for 10 minutes, and then the reaction solvent was removed. The resin was washed with DMF (4.5 mL, 4 times), giving Fmoc-His(Trt)-Asn(Trt)-Phe-O-Trt(2-Cl)-resin.
(5) Subsequently, the deprotection and the Fmoc amino acid-coupling were repeated in accordance with the operations (2) to (4) (coupling reactions were performed by reaction with MW irradiation at 75° C. for 5 minutes except for the coupling of Fmoc-His(Trt)-OH).
(6) Fmoc-Glu(tBu)-OH as the 16th residue was coupled, then the Fmoc group was deprotected, and the resin was washed with dichloromethane and MeOH and was dried under reduced pressure, giving 16-residue peptide-resin.

Figure 15:
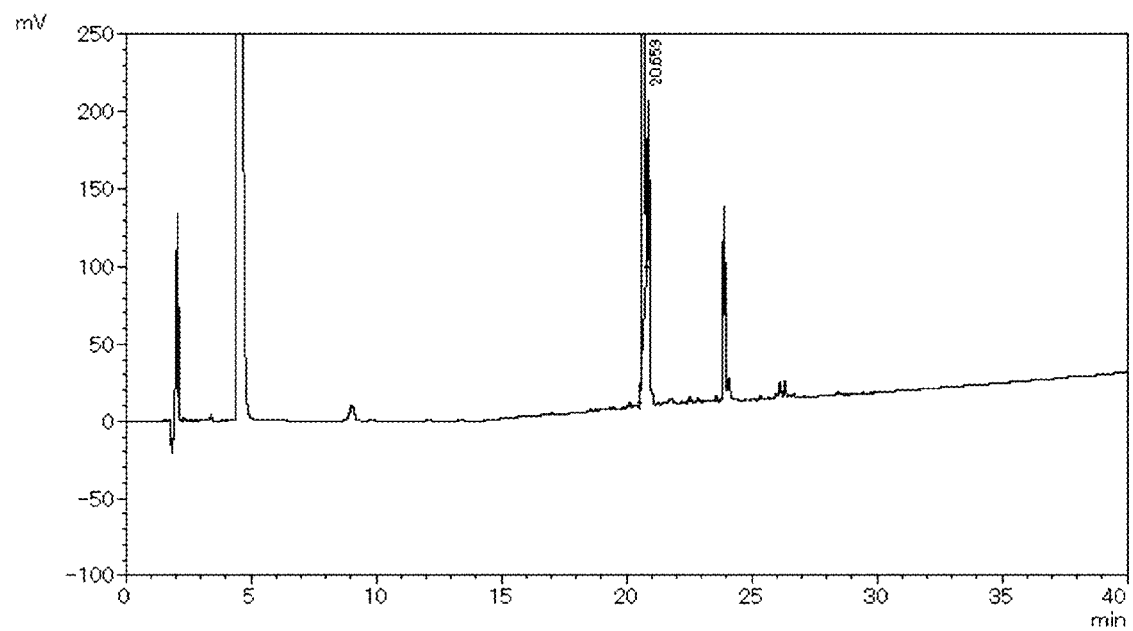
FIG. 15 is an HPLC chromatogram of a product in Experimental Example 7.

4. Cleavage of Deprotected Peptide from Resin and Purity Measurement
(7) To a sample (about 20 mg) of the 16-residue peptide-resin, TFA/TIS/H$_2$O/EDT (TFA/TIS/H$_2$O/EDT=92.5/2.5/2.5/2.5 in terms of volume) (2 mL) was added, and the whole was stirred for 2 hours. After filtration, TFA was evaporated off, then ethyl acetate and water was added, and the mixture was allowed to separate into two layers. The aqueous layer was collected and was washed with ethyl acetate (twice). The aqueous layer was diluted with purified water and was analyzed by HPLC (HPLC purity: 63.4%) (see FIG. 15 and Table 13, gradient program C).

Experimental Example 8

Synthesis of B-Fragment-Resin (H-Lys(Boc)-his(Trt)-Leu-Asn(Trt)-Ser(tBu)-Met-Glu(tBu)-Arg(Pbf)-Val-Glu(tBu)-Trp(Boc)-Leu-Arg(Pbf)-Lys(Boc)-Lys(Boc)-Leu-Gln(Trt)-Asp(tBu)-Val-His(Trt)-Asn(Trt)-Phe-O-Trt(2-Cl)-Resin) (Side Chain-Protected BFR-Resin) (Using an M-Revo (Registered Trademark))

1. Introduction of Fmoc-Amino Acid to Resin
(1) Under an argon atmosphere, Cl-Trt(2-Cl)-resin (10.0 g), Fmoc-Phe-OH (15.0 g), DIEA (6.75 mL), and dichloroethane (100 mL) were placed in a reaction container. The mixture was stirred using an M-Revo (registered trademark) for 3 hours or more, and then the reaction solvent was removed. DIEA (1.35 mL), MeOH (10 mL), and dichloromethane (70.0 mL) were added, and the mixture was stirred using the M-Revo (registered trademark) for 20 minutes under an argon atmosphere. The mixture was washed with DMF, dichloromethane, and DMF, giving Fmoc-Phe-O-Trt(2-Cl)-resin.

2. Deprotection of Fmoc Group
(2) To the Fmoc-Phe-O-Trt(2-Cl)-resin, a 20% piperidine/DMF solution in such a volume as to enable stirring (about 10 v/w) was added. The mixture was stirred using the M-Revo (registered trademark) for 20 minutes, and then the reaction solvent was removed. The residue was washed with DMF, dichloromethane, and DMF, giving H-Phe-O-Trt(2-Cl)-resin.

3. Coupling Reaction
(3) In a flask, Fmoc-Asn(Trt)-OH (23.1 g), HOBt (5.24 g), DIC (6.00 mL), and DMF (70.0 mL) were placed, and the whole was stirred using an M-Revo (registered trademark) for 30 minutes or more.
(4) The solution prepared in (3) was added to the H-Phe-O-Trt(2-Cl)-resin, and the mixture was stirred using the M-Revo (registered trademark) for 2 hours or more.
(5) The reaction solvent was removed, and the resin was washed with DMF, dichloromethane, and DMF, giving Fmoc-Asn(Trt)-Phe-O-Trt(2-Cl)-resin.
(6) Subsequently, the deprotection and the coupling were repeated in the same manner as in (2) to (5). For the 10th residue (Fmoc-Arg(Pbf)-OH), the 15th residue (Fmoc-Arg(Pbf)-OH), the 17th residue (Fmoc-Met-OH), the 21st residue (Fmoc-His(Trt)-OH), and the 22nd residue (Fmoc-Lys(Boc)-OH), double coupling was performed. For the 16th residue (Fmoc-Glu(tBu)-OH), triple coupling was performed, and for the 19th residue (Fmoc-Arg(Pbf)-OH), quadruple coupling was performed.
(7) After the coupling of Fmoc-Lys(Boc)-OH as the 22nd residue, the Fmoc group was deprotected in the same manner as in (2), and the resin was washed with dichloromethane and MeOH and was dried under reduced pressure, giving side chain-protected BFR-resin (78.48 g).

Figure 16:
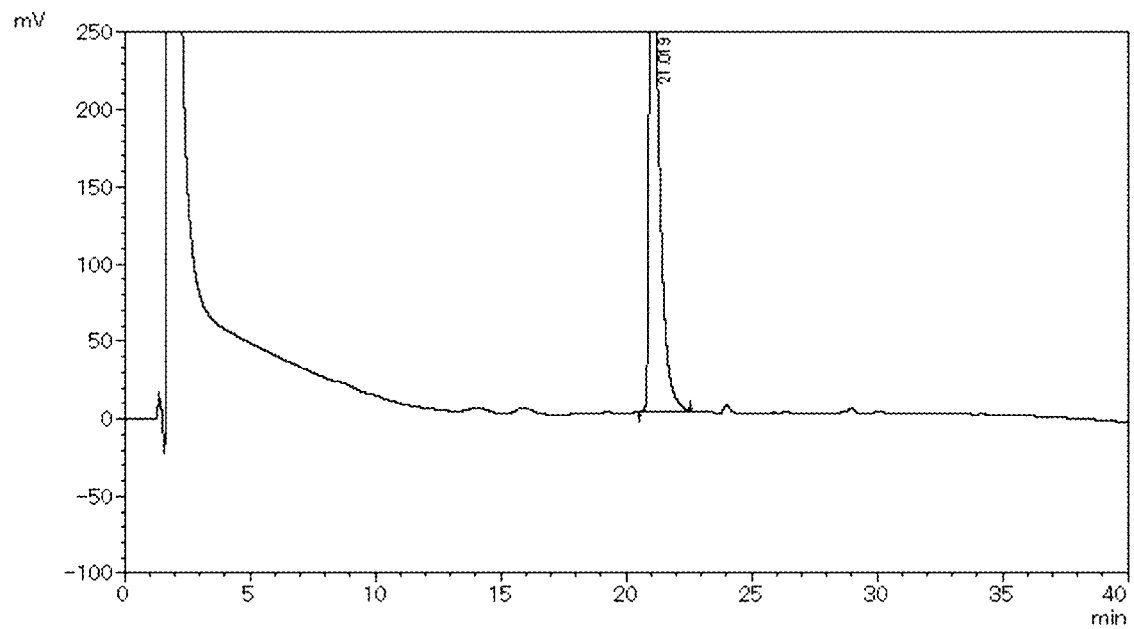
FIG. 16 is an HPLC chromatogram of a product in Experimental Example 8.

4. Cleavage of Protected Peptide from Resin and Purity Measurement
(8) To a sample (about 20 mg) of the side chain-protected BFR-resin, acetic acid/dichloromethane (acetic acid/dichloromethane=1/9 in terms of volume) was added, and the whole was stirred for 2 hours. The reaction solution was diluted with purified water/acetonitrile and was analyzed by HPLC (HPLC purity: 92.0%) (see FIG. 16 and Table 14, gradient program D).

TABLE 14

| Peak | Retention Time (min) | Area % |
|---|---|---|
| B-fragment | 21.02 | 92.034 |

Comparative Example 4

Synthesis of B-Fragment-Resin (H-Lys(Boc)-his(Trt)-Leu-Asn(Trt)-Ser(tBu)-Met-Glu(tBu)-Arg(Pbf)-Val-Glu(tBu)-Trp(Boc)-Leu-Arg(Pbf)-Lys(Boc)-Lys(Boc)-Leu-Gln(Trt)-Asp(tBu)-Val-His(Trt)-Asn(Trt)-Phe-O-Trt(2-Cl)-Resin) (Side Chain-Protected BFR-Resin) (Using a Shaker)

1. Introduction of Fmoc-Amino Acid to Resin (1) Under an argon atmosphere, Cl-Trt(2-Cl)-resin (2.00 g), Fmoc-Phe-OH (2.5 eq.), DIEA (2.5 eq.), and dichloroethane (about 10 v/w) were placed in a reaction container. The mixture was stirred using a shaker for 3 hours or more, and then the reaction solvent was removed. DIEA (0.5 eq.), MeOH (2.0 mL), and dichloromethane (20 mL) were added, and the whole was stirred using a shaker for 20 minutes. The mixture was washed with DMF (20 mL), giving Fmoc-Phe-O-Trt(2-Cl)-resin.

2. Deprotection of Fmoc Group (2) To the Fmoc-Phe-O-Trt(2-Cl)-resin, a 20% piperidine/DMF solution (14 mL) was added. The mixture was stirred using the shaker for 20 minutes, and then the reaction solvent was removed. The residue was washed with DMF, dichloromethane, and DMF, giving H-Phe-O-Trt(2-Cl)-resin.

3. Coupling Reaction (3) In a flask, Fmoc-Asn(Trt)-OH (2.5 eq.), HOBt (2.5 eq.), DIC (2.5 eq.), and DMF (18.0 mL) were placed, and the whole was stirred using the shaker for 30 minutes or more.

(4) The solution prepared in (3) was added to the H-Phe-O-Trt(2-Cl)-resin, then the whole was stirred using the shaker for 2 hours or more, and the reaction solvent was removed. The resin was washed with DMF (20.0 mL), giving Fmoc-Asn(Trt)-Phe-O-Trt(2-Cl)-resin.

(5) Subsequently, the deprotection and the Fmoc-amino acid coupling were repeated in accordance with the operations (2) to (4).

(6) After the coupling of Fmoc-Lys(Boc)-OH as the 22nd residue, the Fmoc group was deprotected in the same manner as in (2), and the resin was washed with MeOH (20 mL) and was dried under reduced pressure, giving side chain-protected BFR-resin (12.18 g).

4. Cleavage of Protected Peptide from Resin and Purity Measurement (7) To the side chain-protected BFR-resin (7.59 g), a degassed Cleavage mixture (76 mL) was added, and the whole was stirred under an argon atmosphere using the shaker for 2 hours.

(8) The resin was further washed with Cleavage mixture (38 mL) and dichloromethane (76 mL).

(9) To the reaction solution, hexane (760 mL) was added, then the mixture was concentrated under reduced pressure, and dichloromethane (15 mL) was added to dissolve crystals. To the solution, IPE (380 mL) was added to precipitate crystals, and the crystals were collected by pressure filtration.

Figure 17:
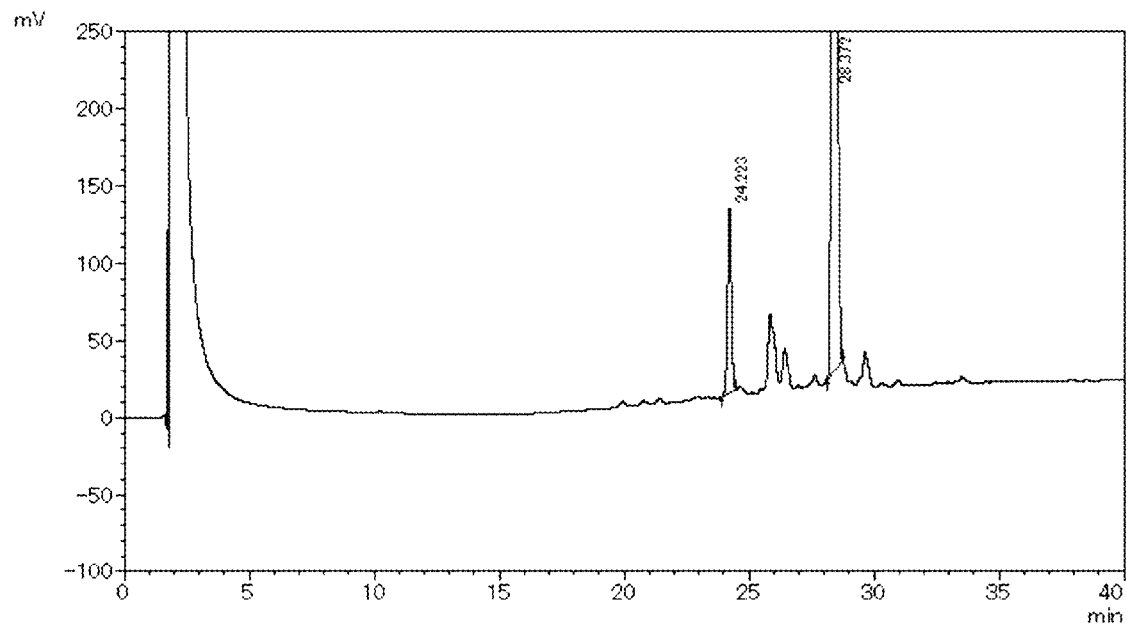
FIG. 17 is an HPLC chromatogram of a product in Comparative Example 4.

(10) The crystals were dried under reduced pressure, then the resulting crystals of the side chain protected B-fragment were dissolved in purified water/acetonitrile, and the solution was analyzed by HPLC (HPLC purity: 63.8%). The results reveal that the target B-fragment has a purity of 63.8% ($t_R$=28.4), whereas the content of the de-tritylated by-product is 9.2% ($t_R$=24.2) (see FIG. 17 and Table 15, gradient program A).

TABLE 15

| Peak | Retention Time (min) | Area % |
|---|---|---|
| de-Tritylated By-product | 24.22 | 9.240 |
| B-fragment | 28.37 | 63.784 |

Comparative Example 5

Synthesis of B-Fragment-Resin (H-Lys(Boc)-his(Trt)-Leu-Asn(Trt)-Ser(tBu)-Met-Glu(tBu)-Arg(Pbf)-Val-Glu(tBu)-Trp(Boc)-Leu-Arg(Pbf)-Lys(Boc)-Lys(Boc)-Leu-Gln(Trt)-Asp(tBu)-Val-His(Trt)-Asn(Trt)-Phe-O-Trt(2-Cl)-Resin) (Side Chain-Protected BFR-Resin) (Using a Fully Automated Microwave Peptide Synthesizer (Initiator+ Alstra Manufactured by Biotage Japan))

1. Introduction of Fmoc-Amino Acid to Resin (1) In a reaction container, H-Phe-O-Trt(2-Cl)-resin (118 mg) and DMF (4.5 mL) were placed, and the resin was allowed to swell for 20 minutes. After removal of the DMF, a 0.5M DMF solution of Fmoc-Asn(Trt)-OH (0.8 mL), a 0.5M DMF solution of DIC (0.8 mL), and a 0.2M DMF solution of HOBt (2.0 mL) were added, then the mixture was reacted by microwave (MW) irradiation at 75° C. for 5 minutes, and the reaction solvent was removed. The resin was washed with DMF (18 mL), giving Fmoc-Asn(Trt)-Phe-O-Trt(2-Cl)-resin.

2. Deprotection of Fmoc Group (2) To the Fmoc-Asn(Trt)-Phe-O-Trt(2-Cl)-resin, a 20% piperidine/DMF solution (4.5 mL) was added, then the whole was stirred for 3 minutes, and the reaction solvent was removed. A 20% piperidine/DMF solution (4.5 mL) was further added, then the whole was stirred for 10 minutes, and the reaction solvent was removed. The resin was washed with DMF (18 mL), giving H-Asn(Trt)-Phe-O-Trt(2-Cl)-resin.

3. Coupling Reaction (3) To the H-Asn(Trt)-Phe-O-Trt(2-Cl)-resin, a 0.5M DMF solution of Fmoc-His(Trt)-OH (0.8 mL), a 0.5M DMF solution of DIC (0.8 mL), and a 0.2M DMF solution of HOBt (2.0 mL) were added.

(4) The whole was reacted by MW irradiation at 50° C. for 10 minutes, and then the reaction solvent was removed. The resin was washed with DMF (18 mL), giving Fmoc-His(Trt)-Asn(Trt)-Phe-O-Trt(2-Cl)-resin.

(5) Subsequently, the deprotection and the Fmoc-amino acid coupling were repeated in accordance with the operations (2) to (4) (coupling reactions were performed by reaction with MW irradiation at 75° C. for 5 minutes except for the coupling of Fmoc-His(Trt)-OH).

(6) After the coupling of Fmoc-Lys(Boc)-OH as the 22nd residue, the Fmoc group was deprotected in the same manner as in (2), and the resin was washed with dichloromethane and MeOH and was dried under reduced pressure, giving side chain-protected BFR-resin.

Figure 18:
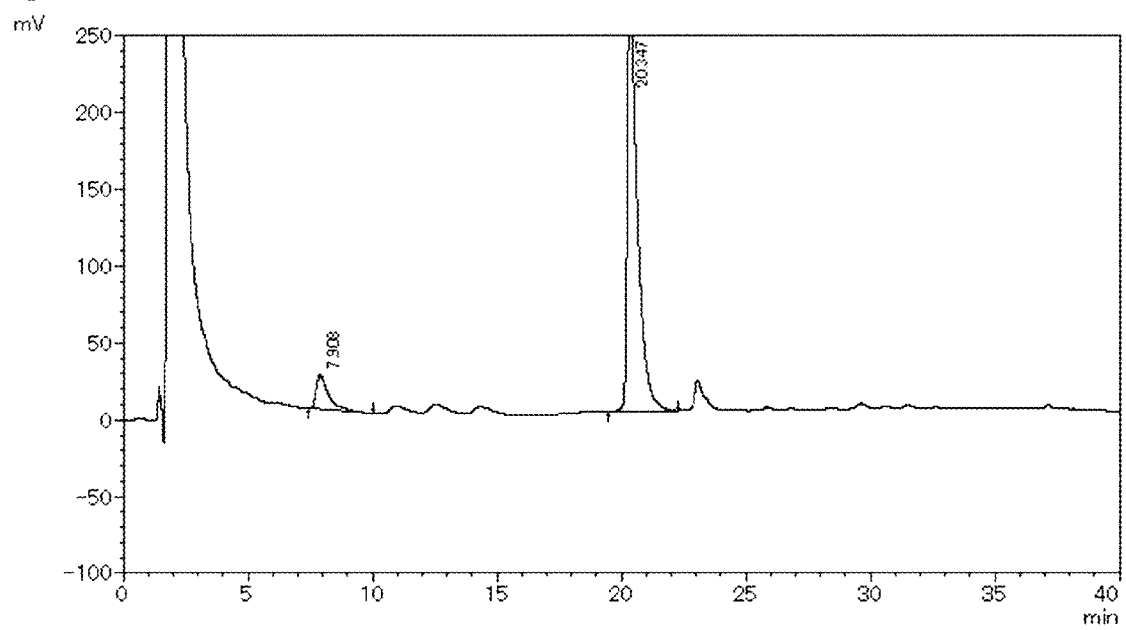
FIG. 18 is an HPLC chromatogram of a product in Comparative Example 5.

4. Cleavage of Protected Peptide from Resin and Purity Measurement (7) To a sample (about 20 mg) of the side chain-protected BFR-resin, Cleavage mixture (2 mL) was added, and the whole was stirred for 2 hours. The reaction solution was diluted with acetonitrile and was analyzed by HPLC. The results reveal that the target B-fragment has a purity of 75.5% ($t_R$=20.4), whereas the content of the de-tritylated by-product is 7.9% ($t_R$=7.9) (see FIG. 18 and Table 16, gradient program D).

TABLE 16

| Peak | Retention Time (min) | Area % |
| --- | --- | --- |
| de-Tritylated By-product | 7.91 | 7.872 |
| B-fragment | 20.35 | 75.518 |

The results of Experimental Examples 5 to 8 and Comparative Examples 3 to 5 are shown in Table 17.

TABLE 17

| Product | | Stirring manner | Scale (initial resin amount) | Purity of target compound (area %) | Content of de-tritylated product |
| --- | --- | --- | --- | --- | --- |
| A-fragment | Experimental Example 5 | M-Revo | 80.0 g | 94.1% | 0.55% |
| | Comparative Example 3 | Fully automated microwave peptide synthesizer | 0.122 g | 66.1% | 7.5% |
| 15-Residue peptide | Experimental Example 6 | Shaker and M-Revo | 4 g (one of two portions divided in process) | 93.1% | — |
| | | Shaker | 4 g (the other of two portions divided in process) | 89.4% | — |
| 16-Residue peptide | Experimental Example 7 | Fully automated microwave peptide synthesizer | 0.179 g | 63.4% | — |
| B-fragment | Experimental Example 8 | M-Revo | 10 g | 92.0% | — |
| | Comparative Example 4 | Shaker | 2 g | 63.8% | 9.2% |
| | Comparative Example 5 | Fully automated microwave peptide synthesizer | 0.118 g | 75.5% | 7.9% |

(In this table, "—" represents "no data".)

The results demonstrate that the production method of the present invention enables mass production of high-purity long-chain peptides. The production method of the present invention is also demonstrated to suppress the generation of a de-tritylated product of an intermediate fragment in solid phase peptide synthesis. In other words, the production method of the present invention is demonstrated to enable mass synthesis of high-purity long-chain peptides while suppressing side reactions.

Experimental Example 9

Synthesis of Pentaalanine (H-Ala-Ala-Ala-Ala-Ala-OH) (Using an M-Revo (Registered Trademark))

1. Introduction of Fmoc-Amino Acid to Resin (1) In a reaction container, Wang resin (para-methoxybenzyl alcohol resin, 5.0 g) and DMF (35 mL) were placed, and the resin was allowed to swell. After removal of the DMF, Fmoc-Ala-OH (2.41 g, 2.5 eq.), HOBt (1.05 g, 2.5 eq.), DMF (35 mL), and DIC (1.2 mL, 2.5 eq.) were added.

(2) The mixture was centrifugal-stirred using an M-Revo (registered trademark) for 2 hours or more.

(3) The reaction solvent was removed, and the Fmoc-Ala-OH-introduced resin was washed using the M-Revo (registered trademark) with DMF (35 mL), dichloromethane (35 mL), and DMF (35 mL).

2. Deprotection of Fmoc Group (4) To the resulting Fmoc-Ala-Wang-resin, 20% piperidine/DMF (35 mL) was added.

(5) The mixture was centrifugal-stirred using the M-Revo (registered trademark) for 20 minutes or more.

(6) The reaction solvent was removed, and the residue was washed using the M-Revo (registered trademark) with DMF (35 mL), dichloromethane (35 mL), and DMF (35 mL).

(7) Kaiser Test was performed to ascertain coloration of the resin beads.

(8) H-Ala-Wang-resin was obtained.

3. Coupling Reaction (9) Into the reaction container in (8), Fmoc-Ala-OH (2.41 g, 2.5 eq.), HOBt (1.05 g, 2.5 eq.), DMF (35 mL), and DIC (1.2 mL, 2.5 eq.) were added.

(10) The mixture was centrifugal-stirred using the M-Revo (registered trademark) for 1 hour or more.

(11) The reaction solvent was removed, and the Fmoc-Ala-OH-introduced resin was washed using the M-Revo (registered trademark) with DMF (35 mL), dichloromethane (35 mL), and DMF (35 mL).

(12) A small amount of the Fmoc-Ala-OH-introduced resin was sampled and subjected to Kaiser Test, and no coloration of the resin beads was detected. If resin beads were colored by Kaiser Test, the operations (9) to (11) were repeated until the resin beads were not colored by Kaiser Test.

(13) The operations (4) to (12) were performed until Boc-Ala-Ala-Ala-Ala-Ala-Wang-resin was obtained. As the N-terminal amino acid, Boc-Ala-OH was introduced.

(14) After the coupling of Boc-Ala-OH, the product was washed with dichloromethane (35 mL) and MeOH (35 mL) and was dried under reduced pressure, giving the following Boc-Ala-Ala-Ala-Ala-Ala-Wang-resin.

[Chemical Formula 4]

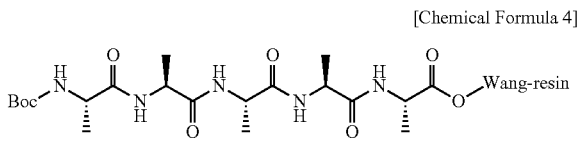

4. Cleavage of Peptide from Resin

(15) To the Boc-Ala-Ala-Ala-Ala-Ala-Wang-resin, TFA/TIS/H$_2$O (TFA/TIS/H$_2$O=95/2.5/2.5 in terms of volume) (35 mL) was added, and the whole was shaken for 2 hours.

(16) The reaction solution was concentrated under reduced pressure and crystallized with IPE (250 mL).

(17) The crystals were filtered under reduced pressure.

(18) The crystals were dried at room temperature under reduced pressure, giving the following H-Ala-Ala-Ala-Ala-Ala-OH.TFA salt (604 mg).

[Chemical Formula 5]

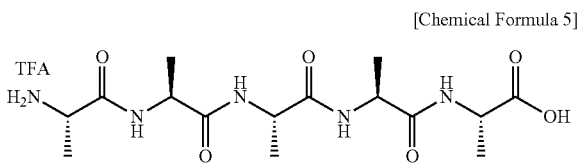 [SMILES: C[C@H](N)C(=O)N[C@@H](C)C(=O)N[C@@H](C)C(=O)N[C@@H](C)C(=O)N[C@@H](C)C(=O)O]

Comparative Example 6

Synthesis of Pentaalanine (H-Ala-Ala-Ala-Ala-Ala-OH) (Using a Shaker)

1. Introduction of Fmoc-Amino Acid to Resin (1) In a reaction container, Wang-resin (0.50 g) and DMF (5 mL) were placed, and the resin was allowed to swell. After removal of the DMF, Fmoc-Ala-OH (775 mg, 6 eq.), HOBt (337 mg, 6 eq.), DMF (2.5 mL), and DIC (386 µL, 6 eq.) were added.

(2) The mixture was shaken using a shaker for 2 hours or more.

(3) The reaction solvent was removed, and the Fmoc-Ala-OH-introduced resin was washed using a shaker with DMF (5 mL), dichloromethane (5 mL), and DMF (5 mL).

2. Deprotection of Fmoc Group (4) To the resulting Fmoc-Ala-Wang-resin, 20% piperidine/DMF (5.5 mL) was added.

(5) The mixture was shaken using a shaker for 20 minutes or more.

(6) The reaction solvent was removed, and the residue was washed using a shaker with DMF (5 mL), dichloromethane (5 mL), and DMF (5 mL).

(7) Kaiser test was performed to ascertain coloration of the resin beads.

(8) H-Ala-Wang-resin was obtained.

3. Coupling Reaction (9) Into the reaction container in (8), Fmoc-Ala-OH (386 mg, 2.5 eq.), HOBt (168 mg, 2.5 eq.), DMF (5.5 mL), and DIC (206 µL, 2.5 eq.) were added.

(10) The mixture was shaken using a shaker for 1 hour or more.

(11) The reaction solvent was removed, and the Fmoc-Ala-OH-introduced resin was washed using a shaker with DMF (5 mL), dichloromethane (5 mL), and DMF (5 mL).

(12) A small amount of the Fmoc-Ala-OH-introduced resin was sampled and subjected to Kaiser Test, and no coloration of the resin beads was detected. If resin beads were colored by Kaiser Test, the operations (9) to (11) were repeated until the resin beads were not colored by Kaiser Test.

(13) The operations (4) to (12) were performed until Boc-Ala-Ala-Ala-Ala-Ala-Wang-resin was obtained. The protected amino acid (N-terminal amino acid) used for the last coupling reaction was Boc-Ala-OH.

(14) After the coupling of Boc-Ala-OH, the product was washed with dichloromethane (5 mL) and MeOH (5 mL) and was dried under reduced pressure, giving Boc-Ala-Ala-Ala-Ala-Ala-Wang-resin (0.68 g).

4. Cleavage of Deprotected Peptide from Resin

(15) To the Boc-Ala-Ala-Ala-Ala-Ala-Wang-resin, TFA/TIS/H$_2$O (TFA/TIS/H$_2$O=95/2.5/2.5 in terms of volume) (5 mL) was added, and the whole was shaken for 2 hours.

(16) After removal of the resin, the reaction solution was concentrated under reduced pressure, and to the residue, IPE (25 mL) was added to precipitate crystals.

(17) The crystals were filtered under reduced pressure.

(18) The crystals were dried at room temperature under reduced pressure, giving H-Ala-Ala-Ala-Ala-Ala-OH.TFA salt (60.7 mg).

HPLC Analysis (Experimental Example 9 and Comparative Example 6)

Figure 19:
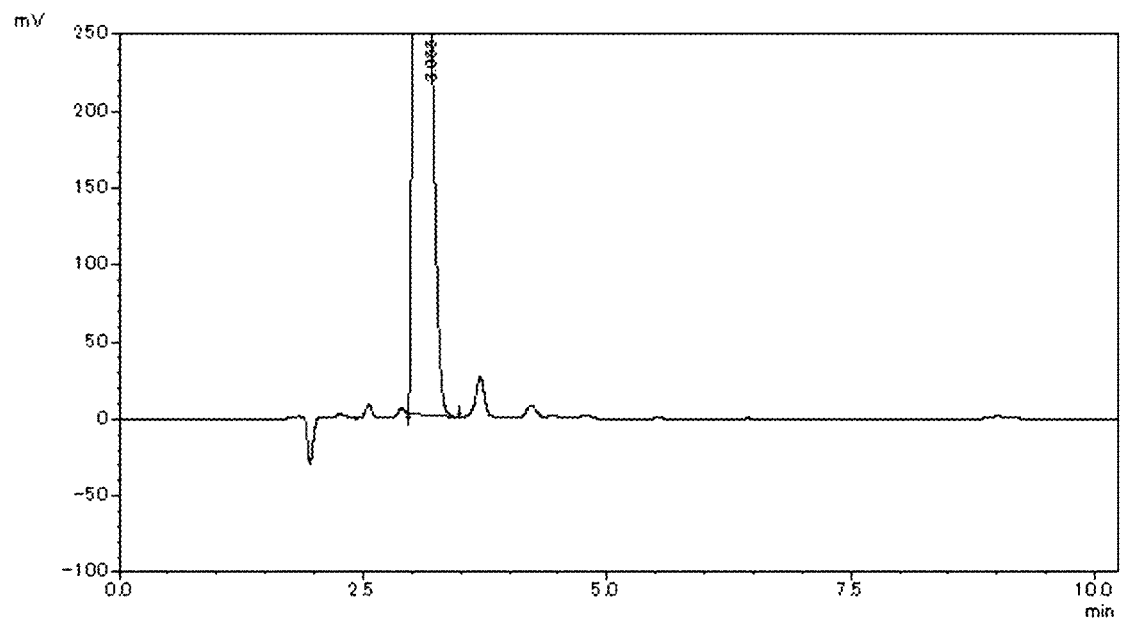
FIG. 19 is an HPLC chromatogram of a product in Experimental Example 9.
Figure 20:
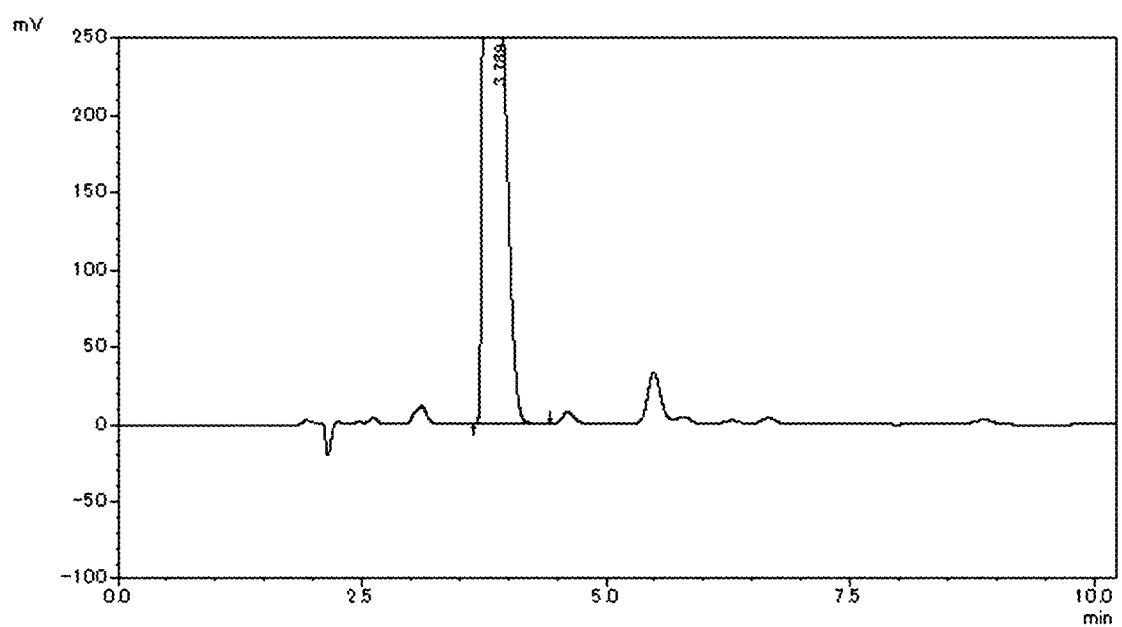
FIG. 20 is an HPLC chromatogram of a product in Comparative Example 6.

The HPLC analysis results of acetonitrile solutions of the products of Experimental Example 9 and Comparative Example 6 are shown in Table 17 and FIGS. 19 and 20. Table 17 shows retention times and contents of the products (pentaalanine) of Experimental Example 9 and Comparative Example 6 in acetonitrile solutions by HPLC analysis. FIGS. 19 and 20 show HPLC chromatograms of acetonitrile solutions of the products of Experimental Example 9 and Comparative Example 6, respectively. The HPLC analysis was performed in the following HPLC conditions.

HPLC conditions
Column: Waters X Bridge
Mobile phase: 0.1% aqueous TFA
Analysis time: about 10 minutes
Flow rate: 1 mL/min
Detector: UV 220 nm

TABLE 18

| Example | Stirring manner | HPLC purity (area %) |
| --- | --- | --- |
| Comparative Example 6 | Shaker | 91.52 |
| Example 9 | M-Revo | 95.85 |

The results demonstrate that the production method of the present invention enables mass production of high-purity long-chain peptides.

INDUSTRIAL APPLICABILITY

The production method of the present invention is useful for peptide production. The method is specifically useful for mass synthesis of a long-chain peptide while suppressing side reactions.

DESCRIPTION OF REFERENCE NUMERALS 1 stirring rotor
5 stirrer main body
10 main body
11 rotating drive shaft
12 inlet port
13 cylindrical rotary member
13A top plate
13B bottom plate
14 outlet port
16 flow path
18 joint
20 drive shaft
21 cylindrical casing
22A to 22D discharge opening
23 suction cylinder
24A to 24D projecting extruded plate
25A to 25D suction opening
30 through hole
38 stirring apparatus
40 stirring rotor
41 stirring rotor main body
41a substantially circular top face of a stirring rotor main body
41b substantially circular bottom face of a stirring rotor main body
41c lateral face as the outer peripheral face of a stirring rotor main body
42 stirring rotor inlet port
44 stirring rotor outlet port
46 stirring rotor flow path
48 joint
50 flow resistor
51 flow resistor main body
51a substantially circular top face of a flow resistor main body
51b substantially circular bottom face of a flow resistor main body
51c lateral face as the outer peripheral face of a flow resistor main body
52 flow resistor inlet port
54 flow resistor outlet port
56 flow resistor flow path
60 drive shaft
a rotating drive shaft rotation direction
b cylindrical rotary member rotation direction
d1, d4 outer discharge flow
e1 to e3 suction flow
g1 to g4, h1 to h4 suction flow
C, L central axis

The invention claimed is:

1. A method for producing a peptide, the method comprising:
performing a solid-phase synthesis while stirring with a centrifugal stirrer having no impeller, wherein the centrifugal stirrer having no impeller is a stirring rotor comprising:
a main body configured to rotate about a rotating shaft,
an inlet port provided on a surface of the main body,
an outlet port provided on the surface of the main body, and
a flow path connecting the inlet port to the outlet port, wherein
the inlet port is provided closer to the rotating shaft than the outlet port, and
the outlet port is provided more distant from the rotating shaft in a centrifugal direction than the inlet port.

2. The method according to claim 1, wherein the peptide has between 5 and 150 amino acid residues.

3. The method according to claim 1, wherein the peptide is a side-chain protected peptide comprising a protecting group.

4. The method according to claim 3, wherein the protecting group is a trityl group.

5. The method according to claim 3, wherein the peptide comprises less than, or equal to, 5% of a de-protected product, where percentage is based on an amount of de-protected product and protected product.

6. The method according to claim 5, wherein the de-protected product is a de-tritylated product.

7. A solid phase peptide synthesis reaction container comprising a centrifugal stirrer having no impeller, wherein the reaction container comprises a glass filter, wherein the centrifugal stirrer having no impeller is a stirring rotor comprising:
a main body configured to rotate about a rotating shaft,
an inlet port provided on a surface of the main body,
an outlet port provided on the surface of the main body, and
a flow path connecting the inlet port to the outlet port, wherein
the inlet port is provided closer to the rotating shaft than the outlet port, and
the outer port is provided more distant from the rotating shaft in a centrifugal direction than the inlet port.

8. A method for suppressing undesired deprotection of a side-chain protected peptide during a solid phase peptide synthesis comprising performing the synthesis in the reaction container according to claim 7.

9. The solid phase peptide synthesis reaction container of claim 7, wherein the reaction container comprises a heating medium jacket.

10. The solid phase peptide synthesis reaction container of claim 7, wherein the reaction container comprises a cock.

* * * * *